US008729036B2

(12) United States Patent
Zamore et al.

(10) Patent No.: US 8,729,036 B2
(45) Date of Patent: May 20, 2014

(54) COMPOSITIONS FOR RNA INTERFERENCE AND METHODS OF USE THEREOF

(75) Inventors: Phillip D. Zamore, Northboro, MA (US); György Hutvágner, Worcester, MA (US); Dianne Schwarz, Worcester, MA (US); Guiliang Tang, Worcester, MA (US); Benjamin Haley, Chelmsford, MA (US)

(73) Assignee: University of Massachusetts, Boston, MA (US)

( * ) Notice: Subject to any disclaimer, the term of this patent is extended or adjusted under 35 U.S.C. 154(b) by 1367 days.

(21) Appl. No.: 10/638,253

(22) Filed: Aug. 7, 2003

(65) Prior Publication Data

US 2004/0203145 A1   Oct. 14, 2004

Related U.S. Application Data

(60) Provisional application No. 60/401,902, filed on Aug. 7, 2002, provisional application No. 60/408,786, filed on Sep. 5, 2002.

(51) Int. Cl.
*C12N 15/11* (2006.01)
*C07H 21/04* (2006.01)

(52) U.S. Cl.
USPC ........................................ 514/44 A; 536/24.5

(58) Field of Classification Search
USPC ............ 514/44; 435/4, 6, 375; 536/23.1, 24.5
See application file for complete search history.

(56) References Cited

U.S. PATENT DOCUMENTS

| | | | |
|---|---|---|---|
| 4,469,863 A | | 9/1984 | Ts'o et al. |
| 5,702,925 A | * | 12/1997 | Smith et al. ................... 435/91.1 |
| 5,898,031 A | | 4/1999 | Crooke |
| 5,998,203 A | * | 12/1999 | Matulic-Adamic et al. ... 435/325 |
| 6,107,094 A | | 8/2000 | Crooke |
| 6,475,726 B1 | | 11/2002 | Tally et al. |
| 6,506,559 B1 | * | 1/2003 | Fire et al. ........................... 435/6 |
| 6,531,647 B1 | | 3/2003 | Baulcombe et al. |
| 6,573,099 B2 | | 6/2003 | Graham |
| 2002/0086356 A1 | | 7/2002 | Tuschl et al. |
| 2002/0132257 A1 | | 9/2002 | Giordano et al. |
| 2002/0137210 A1 | | 9/2002 | Churikov |
| 2002/0150945 A1 | | 10/2002 | Finney et al. |
| 2002/0160393 A1 | | 10/2002 | Symonds et al. |
| 2002/0162126 A1 | | 10/2002 | Beach et al. |
| 2003/0051263 A1 | | 3/2003 | Fire et al. |
| 2003/0055020 A1 | | 3/2003 | Fire et al. |
| 2003/0056235 A1 | | 3/2003 | Fire et al. |
| 2003/0084471 A1 | | 5/2003 | Beach et al. |
| 2003/0108923 A1 | * | 6/2003 | Tuschl et al. ........................ 435/6 |
| 2003/0124513 A1 | | 7/2003 | McSwiggen |
| 2003/0143732 A1 | * | 7/2003 | Fosnaugh et al. ............. 435/325 |
| 2003/0153521 A1 | | 8/2003 | McSwiggen |
| 2003/0170891 A1 | | 9/2003 | McSwiggen |
| 2003/0175950 A1 | | 9/2003 | McSwiggen |
| 2003/0190635 A1 | | 10/2003 | McSwiggen |
| 2003/0190654 A1 | | 10/2003 | Heidenreich et al. |
| 2003/0206887 A1 | | 11/2003 | Morrissey et al. |
| 2004/0001811 A1 | | 1/2004 | Kreutzer et al. |
| 2004/0002077 A1 | | 1/2004 | Taira et al. |
| 2004/0002153 A1 | | 1/2004 | Monia et al. |
| 2004/0005593 A1 | | 1/2004 | Lorens |
| 2004/0006035 A1 | | 1/2004 | Macejak et al. |
| 2004/0018999 A1 | | 1/2004 | Beach et al. |
| 2004/0019001 A1 | | 1/2004 | McSwiggen |
| 2004/0023390 A1 | | 2/2004 | Davidson et al. |
| 2004/0038921 A1 | | 2/2004 | Kreutzer et al. |
| 2004/0053875 A1 | | 3/2004 | Kreutzer et al. |
| 2004/0053876 A1 | | 3/2004 | Turner et al. |
| 2004/0072779 A1 | | 4/2004 | Kreutzer et al. |
| 2004/0086884 A1 | | 5/2004 | Beach et al. |
| 2004/0096843 A1 | | 5/2004 | Rossi et al. |
| 2004/0102408 A1 | | 5/2004 | Kreutzer et al. |
| 2004/0110296 A1 | | 6/2004 | Vargeese et al. |
| 2004/0121348 A1 | | 6/2004 | Kreutzer et al. |
| 2004/0126791 A1 | | 7/2004 | Wajant et al. |
| 2004/0137471 A1 | | 7/2004 | Vickers et al. |
| 2004/0175703 A1 | | 9/2004 | Kreutzer et al. |
| 2004/0180351 A1 | * | 9/2004 | Giese et al. ....................... 435/6 |
| 2004/0191905 A1 | | 9/2004 | Stevenson et al. |
| 2004/0192626 A1 | | 9/2004 | McSwiggen et al. |
| 2004/0192629 A1 | | 9/2004 | Xu et al. |
| 2004/0203145 A1 | | 10/2004 | Zamore et al. |
| 2004/0214198 A1 | | 10/2004 | Rana |

(Continued)

FOREIGN PATENT DOCUMENTS

EP          1214945 B1     6/2002
WO     WO-94/01550 A1     1/1994

(Continued)

OTHER PUBLICATIONS

Boutla et al, Nov. 13, Current Biology 11: 1776-1780, 2001. * of record in specification.*
Tijsterman et al, Jan. 25, Science 295: 694-697, 2002. * of record in specification.*
Chirila et al, January, Biomaterials 23:321-342, 2002.*
Jen et al, Stem Cells 18: 307-319, 2000.*
Stein, C.A., Pharmacol. and Therap. 85: 231-236, 2000.*
Opalinska et al., Nature Reviews 1: 503-514, 2002.*
Scherer et al, Nature Biotechnology 21(12): 1457-1465, 2003.*
Kurreck et al, Current Opinion Drug Discovery and Development 7(2): 179-187, 2004.*
Lu et al, RNA Interference Technology, Cambridge, Appasani, ed., 2005.*
Samarsky et al, RNA Interference Technology, Cambridge, Appasani, ed., 2005.*
Sioud, RNA Silencing, Methods and Protocols, Humana Press, 2005.*

(Continued)

*Primary Examiner* — Dana Shin
(74) *Attorney, Agent, or Firm* — Nelson Mullins Riley & Scarborough LLP; Debra J. Milasincic, Esq.

(57) ABSTRACT

The present invention provides compositions for RNA interference and methods of use thereof. In particular, the invention provides single-stranded small interfering RNAs. Functional and genomic and proteomic methods are featured. Therapeutic methods are also featured.

11 Claims, 8 Drawing Sheets

(56) References Cited

U.S. PATENT DOCUMENTS

| | | | |
|---|---|---|---|
| 2004/0214330 A1 | 10/2004 | Waterhouse et al. |
| 2004/0219516 A1 | 11/2004 | Bennett et al. |
| 2004/0219671 A1 | 11/2004 | McSwiggen et al. |
| 2004/0224328 A1 | 11/2004 | Prydz et al. |
| 2004/0229266 A1 | 11/2004 | Tuschl et al. |
| 2004/0231016 A1 | 11/2004 | Wang et al. |
| 2004/0241854 A1 | 12/2004 | Davidson et al. |
| 2004/0248296 A1 | 12/2004 | Beresford et al. |
| 2004/0248835 A1 | 12/2004 | Krebs et al. |
| 2004/0259247 A1 | 12/2004 | Tuschl et al. |
| 2004/0259248 A1 | 12/2004 | Tuschl et al. |
| 2005/0026278 A1 | 2/2005 | Tuschl et al. |
| 2005/0059005 A1 | 3/2005 | Tuschl et al. |
| 2005/0234006 A1 | 10/2005 | Tuschl et al. |
| 2005/0234007 A1 | 10/2005 | Tuschl et al. |
| 2006/0166910 A1 | 7/2006 | Tuschl et al. |
| 2007/0003960 A1 | 1/2007 | Tuschl et al. |
| 2007/0003962 A1 | 1/2007 | Tuschl et al. |
| 2007/0003963 A1 | 1/2007 | Tuschl et al. |

FOREIGN PATENT DOCUMENTS

| | | | |
|---|---|---|---|
| WO | WO-97/11170 A1 | 3/1997 |
| WO | WO-98/53083 A1 | 11/1998 |
| WO | WO-99/32619 A1 | 7/1999 |
| WO | WO-00/01846 A2 | 1/2000 |
| WO | WO-00/44895 A1 | 8/2000 |
| WO | WO-00/63364 A2 | 10/2000 |
| WO | WO-01/68836 A2 | 9/2001 |
| WO | WO-01/75164 A2 | 10/2001 |
| WO | WO-01/92513 A1 | 12/2001 |
| WO | WO-02/44321 A2 | 6/2002 |
| WO | WO-02/055692 A2 | 7/2002 |
| WO | WO-02/059300 A2 | 8/2002 |
| WO | WO-03/006477 A1 | 1/2003 |
| WO | WO-03/029459 A2 | 4/2003 |
| WO | WO-03/033700 A1 | 4/2003 |
| WO | WO-03/062394 A2 | 7/2003 |
| WO | WO-03/064621 A2 | 8/2003 |
| WO | WO 03/070918 A2 | 8/2003 |
| WO | WO-03/074654 A2 | 9/2003 |
| WO | WO-03/103600 A2 | 12/2003 |
| WO | WO-03/106630 A2 | 12/2003 |
| WO | WO-03/106631 A2 | 12/2003 |
| WO | WO 03099298 A1 * | 12/2003 |
| WO | WO-2004/007718 A2 | 1/2004 |
| WO | WO-2004/014933 A1 | 2/2004 |
| WO | WO-2004/027030 A2 | 4/2004 |
| WO | WO-2004/029212 A2 | 4/2004 |
| WO | WO-2004/042029 A2 | 5/2004 |
| WO | WO-2004/044131 A2 | 5/2004 |
| WO | WO-2004/045543 A2 | 6/2004 |
| WO | WO-2004/046324 A2 | 6/2004 |
| WO | WO-2004/063375 A1 | 7/2004 |
| WO | WO-2004/065600 A2 | 8/2004 |
| WO | WO-2004/065613 A2 | 8/2004 |
| WO | WO-2004/076622 A2 | 9/2004 |
| WO | WO-2004/111191 A2 | 12/2004 |

OTHER PUBLICATIONS

Simeoni et al, RNA Silencing, Methods and Protocols, Humana Press, 2005.*
Mahato et al, Expert Opinion on Drug Delivery (1): 3-28, 2005.*
Tajsharghi et al, Ann. Neurol. 58(3): 442-448, 2005. Abstract only.*
Tuschl et al., Small interfering RNAs: A revolutionary tool for the analysis of gene function and gene therapy, Jun. 2002, Molecular Interventions, vol. 2, pp. 158-167.*
Bryan R. Cullen, RNA interference: antiviral defense and genetic tool, Jul. 2002, Nature Immunology, vol. 3, pp. 597-599.*
Charlie Schmidt, Negotiating the RNAi patent thicket, Mar. 2007, Nature Biotechnology, vol. 25, pp. 273-275.*
Ahlquist, Paul, "RNA-Dependent RNA Polymerases, Viruses, and RNA Silencing," *Science*, vol. 296:1270-1273 (2002).
Ambros, Victor et al, "MicroRNAs and Other Tiny Endogenous RNAs in *C. elegans*," *Current Biology*, vol. 13:807-818 (2003).
Ambros, Victor, "microRNAs: Tiny Regulators with Great Potential," *Cell*, vol. 107:823-826 (2001).
Bass, Brenda L., "Double-Stranded RNA as a Template for Gene Silencing," *Cell*, vol. 101: 235-238 (2000).
Bernstein, Emily et al, "Role for a bidentate ribonuclease in the initiation step of RNA interference," *Nature*, vol. 409:363-366 (2001).
Brummelkamp, Thijn R. et al, "A System for Stable Expression of Short Interfering RNAs in Mammalian Cells," *Science*, vol. 296:550-553 (2002).
Caplen, Natahsa J. et al, "Specific inhibition of gene expression by small double-stranded RNAs in invertebrate and vertebrate systems," *PNAS*, vol. 98(17):9742-9747 (2001).
Carrington, James C. et al, "Role of MicroRNAs in Plant and Animal Development," *Science*, vol. 301:336-338 (2003).
Castanotto, Daniela et al, "Functional siRNA expression from transfected PCR products," *RNA*, vol. 8:1454-1460 (2002).
Chiu, Ya-Lin et al, "RNAi in Human Cells: Basic Structural and Functional Features of Small Interfering RNA," *Molecular Cell*, vol. 10:549-561 (2002).
Chiu, Ya-Lin et al, "siRNA function in RNAi: A chemical modification analysis," *RNA*, vol. 9:1034-1048 (2003).
Cullen, Bryan R., "Derivation and function of small interfering RNAs and microRNAs," *Virus Research*, vol. 102:3-9 (2004).
Devroe, Eric et al, "Retrovirus-delivered siRNA," *BMC Biotechnology*, vol. 2:1-5 (2002).
Doench, John G. et al, "siRNAs can function as miRNAs," *Genes & Development*, vol. 17:438-442 (2003).
Donzé, Olivier et al, "RNA interference in mammalian cells using siRNAs synthesized with T7 RNA polymerase," *Nucleic Acids Research*, vol. 30(10):1-4 (2002).
Dostie, Josée et al, "Numerous microRNPs in neuronal cells containing novel microRNAs," *RNA*, vol. 9:180-186 (2003).
Elbashir, Sayda M. et al, "Duplexes 21-nucleotide RNAs mediate RNA interference in cultured mammalian cells," *Nature*, vol. 411:494-498 (2001).
Elbashir, Sayda M. et al, "Functional anatomy of siRNAs for mediating efficient RNAi in *Drosophila melanogaster* embryo lysate," *The EMBO Journal*, vol. 20(23):6877-6888 (2001).
Elbashir, Sayda M. et al, "RNA interference is mediated by 21- and 22-nucleotide RNAs," *Genes & Development*, vol. 15:188-200 (2001).
Essner, Jeffrey J. et al, "Conserved function for embryonic nodal cilia," *Nature*, vol. 418:37-38 (2002).
Garber, Ken, "Prescription RNA," *Technology Review*, retrieved online at: http://www.technologyreview.com/BioTech/wtr_13020,259,p1.html (2002).
Grishok, Alla et al, "RNAi (Nematodse: *Caenorhaabditis elegans*)," *Advances in Genetics*, vol. 46:339-360 (2002).
Hamilton, Andrew J. et al, "A Species of Small Antisense RNA in Posttranscriptional Gene Silencing in Plants," *Science*, vol. 286:950-952 (1999).
Hutvágner, György et al, "RNAi: nature abhors a double-strand," *Current Opinion in Genetics & Development*, vol. 12:225-232 (2002).
Hutvágner, György et al, "A Cellular Function for the RNA-Interference Enzyme Dicer in the Maturation of the *let-7* Small Temporal RNA," *Science*, vol. 293:834-838 (2001).
Lee, Nan Sook et al, "Expression of small interfering RNAs targeted against HIV-1 *rev* transcripts in human cells," *Nature Biotechnology*, vol. 19:500-505 (2002).
Lee, Rosalind C. et al, "An Extensive Class of Small RNAs in *Caenorhabditis elegans*," *Science*, vol. 294:862-864 (2001).
Lipardi, Concetta et al, "RNAi as Random Degradative PCR: siRNA Primers Convert mRNA into dsRNAs that Are Degraded to Generate New siRNAs," *Cell*, vol. 107:297-307 (2001).
Martinez, Javier et al, "Single-Stranded Antisense siRNAs Guide Target RNA Cleavage in RNAi," *Cell*, vol. 110:563-574 (2002).
McManus, Michael T. et al, "Gene Silencing in Mammals by Small Interfering RNAs," *Nature*, vol. 3:737-747 (2002).

(56) References Cited

OTHER PUBLICATIONS

Nykänen, Antti et al, "ATP Requirements and Small Interfering RNA Structure in the RNA Interference Pathway," *Cell*, vol. 107:309-321 (2001).
Parrish, Susan et al, "Functional Anatomy of a dsRNA Trigger: Differential Requirement for the Two Trigger Strands in RNA Interference," *Molecular Cell*, vol. 6:1077-1087 (2000).
Paul, Cynthia P. et al, "Effective expression of small interfering RNA in human cells," *Nature Biotechnology*, vol. 29:505-508 (2002).
Plasterk, Ronald H.A., "RNA Silencing: The Genome's Immune System," *Science*, vol. 296:1263-1265 (2002).
Schwarz, Dianne S. et al, "Evidence that siRNAs Function as Guides, Not Primers, in the *Drosophila* and Human RNAi Pathways," *Molecular Cell*, vol. 10:537-548 (2002).
Schwarz, Dianne S. et al, "Why do miRNAs live in miRNP?" *Genes & Development*, vol. 16:1025-1031 (2002).
Sijen, Titia et al, "On the Role of RNA Amplification in dsRNA-Triggered Gene Silencing," *Cell*, vol. 107:465-476 (2001).
Tijsterman, Marcel et al, "RNA Helicase MUT-14-Dependent Gene Silencing Triggered in *C. elegans* by Short Antisense RNAs," *Science*, vol. 295:694-697 (2002).
Tijsterman, Marcel et al, "The Genetics of RNA Silencing," *Annu. Rev. Genet.*, vol. 36:489-519 (2002).
Tuschl, Thomas, "RNA Interference and Small Interfering RNAs," *Chembiochem*, vol. 2:239-245 (2001).
Yang, Dun et al, "Evidence that processed small dsRNAs may mediate sequence-specific mRNA degradation during RNAi in *Drosophila* embryos," *Current Biology*, vol. 10:1191-1200 (2000).
Yu, Jenn-Yah et al, "RNA interference by expression of short-interfering RNAs and hairpin RNAs in mammalian cells," *PNAS*, vol. 99(9):6047-6052 (2002).
Zamore, Phillip D., "Ancient Pathways Programmed by Small RNAs," *Science*, vol. 296:1265-1269 (2002).
Zamore, Phillip D., "RNA interference: listening to the sound of silence," *Nature Structural Biology*, vol. 8(9):746-750 (2001).
Zamore, Phillip D. et al, "RNAi: Double-Stranded RNA Directs the ATP-Dependent Cleavage of mRNA at 21 to 23 Nucleotide Intervals," *Cell*, vol. 101:25-33 (2000).
Grzelinski, Marius et al, "RNA Interference-Mediated Gene Silencing of Pleiotrophin Through Polyethylenimine-Complexed Small Interfering RNAs In Vivo Exerts Antitumoral Effects in Glioblastoma Xenografts," *Human Gene Therapy*, 17:751-766 (2006).
Hu-Lieskovan, Siwen et al, "Sequence-Specific Knockdown of EWS-FLI1 by Targeted, Nonrival Delivery of Small Interfering RNA Inhibits Tumor Growth in a Murine Model of Metastatic Ewing's Sarcoma," *Cancer Research*, 65:(19) 8984-8992 (2005).
Li, Bao-jian et al, "Using siRNA in Pophylactic and Therapeutic Regimens Against SARS Coronavirus in Rhesus Macaque," *Nature Medicine*, vol. 11:9, 944-951 (2005).
Reich, Samuel J. et al, "Small Interfering RNA (siRNA) targeting VEGF Effectively Inhibits Ocular Neovascularization in a Mouse Model," *Molecular Vision*, vol. 9, 210-216 (2003).
Soutschek, Jurgen et al, "Therapeutic Silencing of an Endogenous Gene by Systemic Administration of Modified si RNAs," *Nature Publishing Group*, vol. 432, 173-178 (2004).
Tan, P. H. et al, "Gene Knockdown with Intrathecal siRNA of NMDA Receptor NR2B Subunit Reduces Formalin-induced Nociception in the Rat," *Gene Therapy*, vol. 12, 59-66 (2005).
Thakker, Deepak R. et al, "Neurochemical and Behavioral Consequences of VVidespred Gene Knockdown in the Adult Mouse Brain by Using Nonrival Interference,",*PNAS*, vol. 101:49, 17270-17275 (2004).
Zhang, Yingjie et al, "Engineering Mucosal RNA Interference in Vivo," *Molecular Therapy*, vol. 14:3, 336-342 (2006).
Zimmermann, Tracy S. et al, "RNAi-mediated Gene Silencing in Non-human Primates," *Nature*, vol. 441, 111-114 (2006).
Amarzguioui, Mohammed et al., "Tolerance for mutations and chemical modifications in a siRNA," *Nucleic Acids Research*, vol. 31(2):589-595 (2003).
Billy, Eric et al., "Specific interference with gene expression induced by long, double-stranded RNA in mouse embryonal teratocarcinoma cell lines," *PNAS*, vol. 98(25):14428-14433 (2001).
Boutla, Alexandra et al., "Short 5'-phosphorylated double-stranded RNAs induce RNA interference in *Drosophila*," *Current Biology*, vol. 11:1776-1780 (2001).
Celotto, Alicia M. et al., "Exon-specific RNAi: A tool for dissecting the functional relevance of alternative splicing," *RNA*, vol. 8:718-724 (2002).
Chiu, Ya-Lin et al., "siRNA function in RNAi: A chemical modification analysis," *RNA*, vol. 9:1034-1048 (2003).
Czauderna, Frank et al., "Structural variations and stabilizing modifications of synthetic siRNAs in mammalian cells," *Nucleic Acids Research*, vol. 31(11):2705-2716 (2003).
Elbashir, Sayda M. et al., "Analysis of gene function in somatic mammalian cells using small interfering RNAs," *Methods*, vol. 26:199-213 (2002).
Grishok, Alla et al., "Genes and Mechanisms Related to RNA Interference Regulate Expression of the Small Temporal RNAs that Control *C. elegans* Developmental Timing," *Cell*, vol. 106:23-34 (2001).
Hammond, Scott M. et al., "An RNA-directed nuclease mediates post-transcriptional gene silencing in *Drosophila* cells," *Nature*, vol. 404:293-296 (2000).
Hammond, Scott M. et al., "Argonaute2, a Link Between Genetic and Biochemical Analyses of RNAi," *Science*, vol. 293:1146-1150 (2001).
Hannon, Gregory J., "RNA interference," *Nature*, vol. 418:244-251 (2002).
Hohjoh, Hirohiko, "RNA interference (RNAi) induction with various types of synthetic oligonucleotide duplexes in cultured human cells," *FEBS Letters*, vol. 521:195-199 (2002).
Holen, Torgeir et al., "Positional effects of short interfering RNAs targeting the human coagulation trigger Tissue Factor," *Nucleic Acids Research*, vol. 30(8):1757-1766 (2002).
Hutvágner, György et al., "A microRNA in a Multiple-Turnover RNAi Enzyme Complex," *Science*, vol. 297:2056-2060 (2002).
Ketting, René F. et al., "Dicer functions in RNA interference and in synthesis of small RNA involved in developmental timing in *C. elegans*," *Genes & Development*, vol. 15:2654-2659 (2001).
Klahre, Ulrich et al., "High molecular weight RNAs and small interfering RNAs induce systemic posttranscriptional gene silencing in plants," *PNAS*, vol. 99(18):11981-11986 (2002).
Knight, Scott W. et al., "A Role for the RNase III Enzyme DCR-1 in RNA Interference and Germ Line Development in *Caenorhabditis elegans*," *Science*, vol. 293:2269-2271 (2001).
Lewis, David L. et al., "Efficient delivery of siRNA for inhibition of gene expression in postnatal mice," *Nature Genetics*, vol. 32:107-108 (2002).
McCaffrey, Anton P. et al., "RNA interference in adult mice," *Nature*, vol. 418(6893):38-39 (2002).
Nishikura, Kazuko, "A Short Primer on RNAi: RNA-Directed RNA Polymerase Acts as a Key Catalyst," *Cell*, vol. 107:415-418 (2001).
Sharp, Phillip A., "RNA interference—2001," *Genes & Development*, vol. 15:485-490 (2001).
Tabara, Hiroaki et al., "The dsRNA Binding Protein RDE-4 Interacts with RDe-1, DCR-1, and a DExH-Box Helicase to Direct RNAi in *C. elegans*," *Cell*, vol. 109:861-871 (2002).
Xia, Haibin et al., "siRNA-mediated gene silencing in vitro and in vivo," *Nature Biotechnology*, vol. 20:1006-1010 (2002).
Zeng, Yan et al., "Both Natural and Designed Micro RNAs Can Inhibit the Expression of Cognate mRNAs When Expressed in Human Cells," *Molecular Cell*, vol. 9:1327-1333 (2002).
Agrawal, S., "Antisense oligonucleotides: towards clinical trials," *Trends in Biotechnology*, vol. 14(10):376-387 (1996).
Agrawal, Neema et al., "RNA Interference: Biology, Mechanism, and Applications," *Microbiology and Molecular Biology Reviews*, vol. 67(4):657-685 (2003).
Bass, Brenda L., "The short answer," *Nature*, vol. 411:428-429 (2001).
Baulcombe, David C., "Gene silencing: RNA makes RNA makes no protein," *Current Biology*, vol. 9:R599-R601 (1999).
Bernstein, Emily et al., "The rest is silence," *RNA*, vol. 7:1509-1521 (2001).

(56) References Cited

OTHER PUBLICATIONS

Biotech Journal, "Small interfering RNAs," retrieved online at www.biotechjournal.com (2002).
Bosher, Julia M. et al., "RNA interference: genetic wand and genetic watchdog," *Nature Cell Biology*, vol. 2:E31-E36 (2000).
Boutla, Alexandra et al., "Developmental defects by antisense-mediated inactivation of micro-RNAs 2 and 13 in *Drosophila* and the identification of putative target genes," *Nucleic Acids Research*, vol. 31(17):4973-4980 (2003).
Branch, Andrea D., "A good antisense molecule is hard to find," TIBS, vol. 23:45-50 (1998).
Brantl, Sabine, "Antisense-RNA regulation and RNA interference," *Biochimica et Biophysica Acta*, vol. 1575:15-25 (2002).
Cameron, F.H. et al., "Inhibition of gene expression by a short sense fragment," Nucleic Acids Research, vol. 19(3):469-475 (1991).
Caplen, Natasha J. et al., "dsRNA-mediated gene silencing in cultured *Drosophila* cells: a tissue culture model for the analysis of RNA interference," Gene, vol. 252:95-105 (2000).
Check, Erika, "RNA to the Rescue?" Nature, vol. 425:10-12 (2003).
Cheng, Jerry C. et al., "RNA interference and human disease," Molecular Genetics and Metabolism, vol. 80:121-128 (2003).
Chi, Jen-Tsan et al., "Genomewide view of gene silencing by small interfering RNAs," PNAS, vol. 100(11):6343-6346 (2003).
Chiu, Ya-Lin et al., "RNAi in Human Cells: Basic Structural and Functional Features of Small Interfering RNA," Molecular Cell, vol. 10:549-561 (2002).
Conte, Darryl Jr. et al., "RAN Interference in *Caenorhabditis elegans*," Current Protocols in Molecular Biology, Unit 26.3, Supplement 62, pp. 26.3.1-26.3.20 (2003).
Couzin, Jennifer, "RNAi Shows Cracks in Its Armor," Science, vol. 306:1124-1125 (2004).
Crooke, Stanley T. et al., "Kinetic characteristics of *Escherichia coli* RNase H1: cleavage of various antisense oligonucleotide-RNA duplexes," Biochem. J., vol. 312:599-608 (1995).
Cullen, Bryan R., "RNA interference: antiviral defense and genetic tool," Nature Immunology, vol. 3(7):597-599 (2002).
Cummins, Lendell L. et al., "Characterization of fully 2'-modified oligoribonucleotide hetero- and homoduplex hybridization and nuclease sensitivity," Nucleic Acids Research, vol. 23(11):2019-2024 (1995).
De Mesmaeker, Alain et al., "Backbone modifications in oligonucleotides and peptide nucleic acid systems," Current Opinion in Structural Biology, vol. 5:343-355 (1995).
DePalma, Angelo et al., "Making Sense of RNA Interference Methods," retrieved online http://www.adepalma.com/genomics/0303/Genomics%20and%20Proteomics%20-%20Making%20Sense%20of%20RNA%20Interference%20Methods.htm (2003).
Doi, Noboru et al., "Short-Interfering-RNA-Mediated Gene Silencing in Mammalian Cells Requires Dicer and dIF2C Translation Initiation Factors," Current Biology, vol. 13:41-46 (2003).
Fire, Andrew et al., "Potent and specific genetic interference by double-stranded RNA in *Caenorhabditis elegans*," Nature, vol. 391:806-811 (1998).
Fire, Andrew, "RNA-triggered gene silencing," TIG, vol. 15(9):358-363 (1999).
Gewirtz, Alan M. et al., "Nucleic Acid Therapeutics: State of the Art and Future Prospects," Blood, vol. 92(3):712-736 (1998).
Gitlin, Leonid et al., "Short interfering RNA confers intracellular antiviral immunity in human cells," Nature, vol. 418:430-434 (2002).
Guo, Su et al., "par-1, a Gene Required for Establishing Polarity in *C. elegans* Embryos, Encodes a Putative Ser/Thr Kinase That Is Asymmetrically Distributed," Cell, vol. 81:611-620 (1995).
Haley, Benjamin et al., "In vitro analysis of RNA interference in *Drosophila melanogaster*," Methods, vol. 30:330-336 (2003).
Hamada, Makiko et al., "Effects of RNA Interference in Gene Expression (RNAi) in Cultured Mammalian Cells of Mismatches and the Introduction of Chemical Modifications at the 3'-Ends of siRNAs," Antisense and Nucleic Acid and Drug Development, vol. 12:301-309 (2002).

Hamilton, Andrew et al., "Two classes of short interfering RNA in RNA silencing," The EMBO Journal, vol. 21(17):4671-4679 (2002).
Hammond, Scott M. et al., "Post-transcriptional Gene Silencing by Double-stranded RNA," Nature, vol. 2:110-119 (2001).
Heinrichs, Arianne, "Chop, chop," Nature, vol. 4:829 (2003).
Heinrichs, Arianne, "Spreading silence," Nature Reviews, Molecular Cell Biology, vol. 4:823 (2003).
Holen, Torgeir et al., "Similar behaviour of single-strand and double-strand siRNAs suggests they act through a common RNAi pathway," Nucleic Acids Research, vol. 31(9):2401-2407 (2003).
Hough, Shelley R. et al., "Why RNAi makes sense," Nature Biotechnology, vol. 21(7):731-732 (2003).
Hunter, Craig P., "Genetics: A touch of elegance with RNAi," Current Biology, vol. 9:R440-R442 (1999).
Hutvágner, György et al., "Detailed characterization of the post-transcriptional gene-silencing-related small RNA in a GUS gene-silenced tobacco," RNA, vol. 6:1445-1454 (2000).
Hutvágner, György et al., "Intersection of the RNA Interference and Small Temporal RNA Pathways," Jun. 29, 2001, Meeting abstract.
Hutvágner, György et al., "In vitro processing of pre-let-7 RNA," RNA Society Meeting, May 31, 2001, poster session II.
Jackson, Aimee L. et al., "Expression profiling reveals off-target gene regulation by RNAi," Nature Biotechnology, vol. 21:635-637 (2003).
Ketting, René F. et al., "A genetic link between co-suppression and RNA interference in *C. elegans*," Nature, vol. 404:296-298 (2000).
Khvorova, Anastasia et al., "Functional siRNAs and miRNAs Exhibit Strand Bias," Cell, vol. 115:209-216 (2003).
Lima, Walt F. et al., "Cleavage of Single Strand RNA Adjacent to RNA-DNA Duplex Regions by *Escherichia coli* RNase H1," The Journal of Biological Chemistry, vol. 272(44):27513-27516 (1997).
Lima, Walt F. et al., "Human RNase H1 Uses NOe Tryptophan and Two Lysines to Position the Enzyme at the 3'-DNA/5'-RNA Terminus of the Heteroduplex Substrate," The Journal of Biological Chemistry, vol. 278(50):49860-49867 (2003).
Lima, Walt F. et al., "The Influence of Antisense Oligonucleotide-induced RNA Structure on *Escherichia coli* RNase H1 Activity," The Journal of Biological Chemistry, vol. 272(29):18191-18199 (1997).
Majlessi, Mahrdad et al., "Advantages of 2'-O-methyl oligoribonucleotide probes for detecting RNA targets," Nucleic Acids Research, vol. 26(9):2224-2229 (1998).
Martinez, Luis Alfonso et al., "Synthetic small inhibiting RNAs: Efficient tools to inactivate oncogenic mutations and restore p53 pathways," PNAS, vol. 99(23):14849-14854 (2002).
Matzke, Marjori et al., "RNAi Extends Its Reach," Science, vol. 301:1060-1061 (2003).
McManus, Michael T. et al., "Small Interfering RNA-Mediated Gene Silencing in T Lymphocytes," The Journal of Immunology, vol. 169:5754-5760 (2002).
Mercola, Dan et al., "Antisense approaches to cancer gene therapy," Cancer Gene Therapy, vol. 2(1):47-59 (1995).
Miyagishi, Makoto et al., "U6 promoter-drive siRNAs with four uridine 3' overhangs efficiently suppress targeted gene expression in mammalian cells," Nature Biotechnology, vol. 19:497-500 (2002).
Molenaar, C. et al., "Linear 2' O-Methyl RNA probes for the visualization of RNA in living cells," Nucleic Acids Research, vol. 29(17):1-9 (2001).
Monia, Brett P. et al., "Evaluation of 2'-Modified Oligonucleotides Containing 2'-Deoxy Gaps as Antisense Inhibitors of Gene Expression," The Journal of Biological Chemistry, vol. 268(19):14514-14522 (1993).
Monia, Brett P. et al., "Selective Inhibition of Mutant Ha-ras mRNA Expression by Antisense Oligonucleotides," The Journal of Biological Chemistry, vol. 267(28):19954-19962 (1992).
Monia, Brett P. et al., "Sequence-specific antitumor activity of a phosphorothioate oligodeoxyribonucleotide targeted to human C-raf kinase supports an antisense mechanism of action in vivo," Proc. Natl. Acad. Sci. USA, vol. 93:15481-15484 (1996).
Mourelatos, Zissimos et al., "miRNPs: a novel class of ribonucleoproteins containing numerous microRNAs," Genes & Development, vol. 16:720-728 (2002).
Myers, Jason W. et al., "Recombinant Dicer efficiently converts large dsRNAs into siRNAs suitable for gene silencing," Nature Biotechnology, vol. 21:324-328 (2003).

(56) References Cited

OTHER PUBLICATIONS

Paddison, Patrick J. et al., "Short hairpin RNAs (shRNAs) induce sequence-specific silencing in mammalian cells," Genes & Development, vol. 16:948-958 (2002).
Paddison, Patrick J. et al., "Stable suppression of gene expression by RNAi in mammalian cells," PNAS, vol. 99(3):1443-1448 (2002).
Persengiev, Stephen P. et al., "Nonspecific, concentration-dependent stimulation and repression of mammalian gene expression by small interfering RNAs (siRNAs)," RNA, vol. 10:12-18 (2004).
Pasquinelli, Amy E. et al., "Conservation of the sequence and temporal expression of let-7 heterochronic regulatory RNA," Nature, vol. 408:86-89 (2000).
Ruvkun, Gary, "Glimpses of a Tiny RNA World," Science, vol. 294:797-799 (2001).
Schmitz, John C. et al., "Effect of 2'-O-methyl antisense ORNs on expression of thymidylate synthase in human colon cancer RKO cells," Nucleic Acids Research, vol. 29(2):415-422 (2001).
Schwarz, Dianne S. et al., "Asymmetry in the Assembly of the RNAi Enzyme Complex," Cell, vol. 115:199-208 (2003).
Sharp, Phillip A., "RNAi and double-stranded RNA," Genes & Development, vol. 13:139-141 (1999).
Shi, Yang, "Mammalian RNAi for the masses," Trends in Genetics, vol. 19(1):9-12 (2003).
Skipper, Magdalena, "Elegant tour de force," Nature Reviews/Genetics, vol. 4:79-80 (2003).
Song, Erwei et al., "RNA interference targeting Fas protects mice from fulminant hepatitis," Nature Medicine, vol. 9(3):347-351 (2003).
Skyba, Danny M. et al., "Direct In Vivo Visualization of Intravascular Destruction of Microbubbles by Ultrasound and its Local Effects on Tissue," Circulation, vol. 98:290-293 (1998).
Steinberg, Douglas, "MicroRNA Shows Macro Potential," The Scientist, vol. 17(12):1-9 (2003).
Stipp, David, "Biotech's Billion Dollar Breakthrough," Fortune, vol. 147(10):96-100 (2003).
Svoboda, Petr et al., "RNAi in Mouse Oocytes and Preimplantation Embryos: Effectiveness of Hairpin dsRNA," Biochemical and Biophysical Research Communications, vol. 287:1099-1104 (2001).
Svoboda, Petr et al., "Selective reduction of dormant material mRNAs in mouse oocytes by RNA interference," Development, vol. 127:4147-4156 (2000).
Szweykowska-Kulińska, Zofiia et al., "RNA interference and its role in the regulation of eucaryotic gene expression," Acta Biochimica Polonica, vol. 50(1):217-229 (2003).
Tang, Guiliang et al., "A biochemical framework for RNA silencing in plants," Genes & Development, vol. 17:49-63 (2003).
Tijsterman, Marcel et al., "PPW-1, a PAZ/PIWI Protein Required for Efficient Germline RNAi, Is Defective in a Natural Isolate of *C. elegans*," Current Biology, vol. 12:1535-1540 (2002).
Tuschl, Thomas, "Expanding small RNA interference," Nature Biotechnology, vol. 20:446-448 (2002).
Tuschl, Thomas, "RNA sets the standard," Nature, vol. 421:220-221 (2003).
Tuschl, Thomas, "RNA Silencing," Upstate Biosignals, vol. 3:1-15 (2003).
Tuschl, Thomas et al., "Targeted mRNA degradation by double-stranded RNA in vitro," Genes & Development, vol. 13:3191-3197 (1999).
Vickers, Timothy A. et al., "Efficient Reduction of Target RNAs by Small Interfering RNA and RNase H-dependent Antisense Agents," The Journal of Biological Chemistry, vol. 278(9):7108-7118 (2003).
Wall, Nathan R. et al., "Small RNA: can RNA interference be exploited for therapy?" The Lancet, vol. 362:1401-1403 (2003).
Wess, Ludger et al., "Managing Complexity: Early Days for RNAi," Compugen, retrieved online at http://www.cgen.com/news.articles/article031703.html (2003).
Yang, Dun et al., "Short RNA duplexes produced by hydrolysis with *Escherichia coli* RNase III mediate effective RNA interference in mammalian cells," PNAS, vol. 99(15):9942-9947 (2002).
Zamore, Phillip D. et al., "siRNAs knock down hepatitis," Nature Medicine, vol. 9(3):266-267 (2003).
Zamore, Phillip D. et al., "Target dependent accumulation of small RNAs during RNAi in *C. elegans*," retrieved online at http://www.wormbase.org/db/misc/paper?name=%5Bwm2001p307%5D;class=Paper, (2001).
Zhang, Haidi et al., "Human Dicer preferentially cleaves dsRNAs at their termini without a requirement for ATP," The EMBO Journal, vol. 21(21):5875-5885 (2002).
International Preliminary Examination Report for Application No. PCT/US03/24768, dated Jun. 1, 2004.
Raponi, Mitch et al., "Dominant genetic screen for cofactors that enhance antisense RNA-mediated gene silencing in fission yeast," *Nucleic Acids Research*, vol. 30(11):2546-2554 (2002).
Raponi, Mitch et al., "Double-stranded RNA-mediated gene silencing in fission yeast," *Nucleic Acids Research*, vol. 31(15):4481-4489 (2003).
Sigova, Alla et al., "A single Argonaute protein mediates both transcriptional and posttranscriptional silencing in *Schizosaccharomyces pombe*," *Genes & Development*, vol. 18:2359-2367 (2004).
Takamizawa, Junichi et al., "Reduced Expression of the *let-7* MicroRNAs in Human Lung Cancers in Association with Shortened Postoperative Survival," *Cancer Research*, vol. 64:3753-3756 (2004).

\* cited by examiner

Fig. 2A

| guide strand length (nt) | guide strand 5' end | guide strand 3' end | siRNA sequence |
|---|---|---|---|
| 21 | OH | OH | 5´-UCGAAGUAUUCCGCGUACGUG-3´ (SEQ ID NO:1)<br>3´-UUAGCUUCAUAAGGCGCAUGC-5´ (SEQ ID NO:2) |
| 21 | CH₃O | OH | 5´-CH₃O-dTCGAAGUAUUCCGCGUACGUG-3´ (SEQ ID NO:3)<br>3´-UUAGCUUCAUAAGGCGCAUGC-5´ (SEQ ID NO:4) |
| 21 | OH | 2´,3´ ddC | 5´-UCGAAGUAUUCCGCGUACGUddC-3´ (SEQ ID NO:5)<br>3´-UUAGCUUCAUAAGGCGCAUGC-5´ (SEQ ID NO:6) |
| 21 | OH | AM | 5´-UCGAAGUAUUCCGCGUACGUG-AM-3´ (SEQ ID NO:7)<br>3´-UUAGCUUCAUAAGGCGCAUGC-5´ (SEQ ID NO:8) |
| 20 | OH | OH | 5´-UCGAAGUAUUCCGCGUACGU-3´ (SEQ ID NO:9)<br>3´-UUAGCUUCAUAAGGCGCAUGC-5´ (SEQ ID NO:10) |
| 20 | OH | 2´,3´ ddC | 5´-UCGAAGUAUUCCGCGUACGddC-3´ (SEQ ID NO:11)<br>3´-UUAGCUUCAUAAGGCGCAUGC-5´ (SEQ ID NO:12) |
| 20 | OH | AM | 5´-UCGAAGUAUUCCGCGUACGU-AM-3´ (SEQ ID NO:13)<br>3´-UUAGCUUCAUAAGGCGCAUGC-5´ (SEQ ID NO:14) |
| 20 | OH | OH | 5´-UCGAAGUAUUCCGCGUACGC-3´ (SEQ ID NO:15)<br>3´-UUAGCUUCAUAAGGCGCAUGC-5´ (SEQ ID NO:16) |
| 19 | OH | OH | 5´-UCGAAGUAUUCCGCGUACG-3´ (SEQ ID NO:17)<br>3´-UUAGCUUCAUAAGGCGCAUGC-5´ (SEQ ID NO:18) |
| 19 | OH | AM | 5´-UCGAAGUAUUCCGCGUACG-AM-3´ (SEQ ID NO:19)<br>3´-UUAGCUUCAUAAGGCGCAUGC-5´ (SEQ ID NO:20) |
| 21 | OH | OH | 5´-UGAGGUAGUAGGUUGUAUAGU-3´ (SEQ ID NO:21)<br>3´-UUACUCCAUCAUCCAACAUAU-5´ (SEQ ID NO:22) |
| 21 | OH, 2´dT | AM | 5´-dTGAGGUAGUAGGUUGUAUAGU-AM-3´ (SEQ ID NO:23)<br>3´-UUACUCCAUCAUCCAACAUAU-5´ (SEQ ID NO:24) |

Fig. 2B

luciferase          let-7

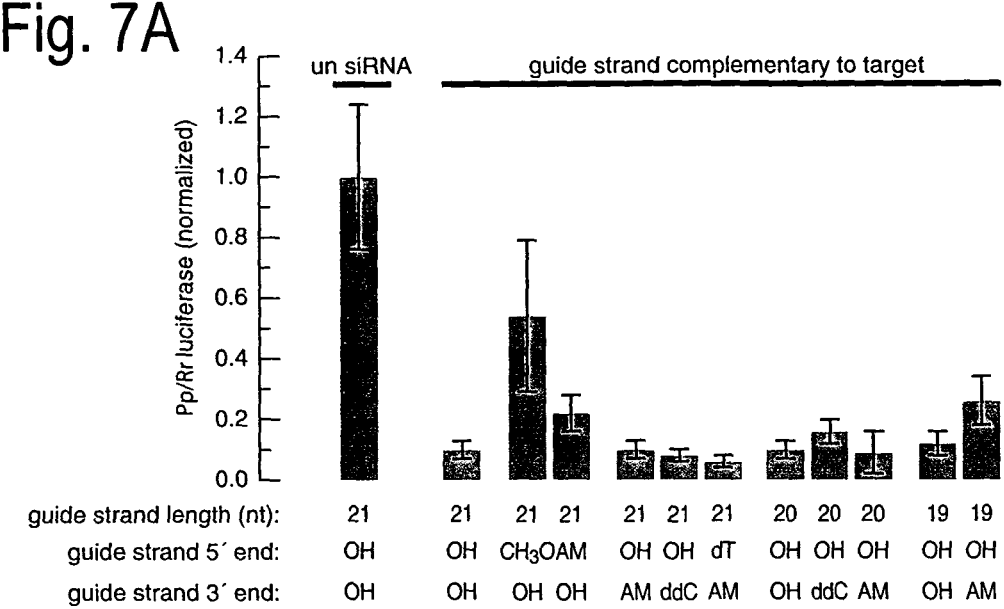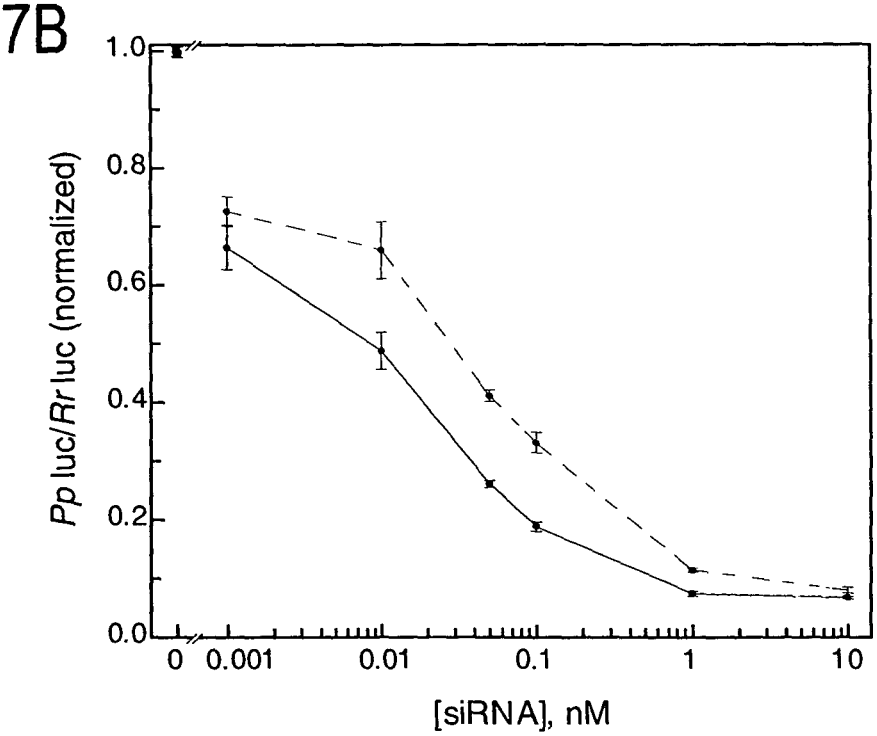

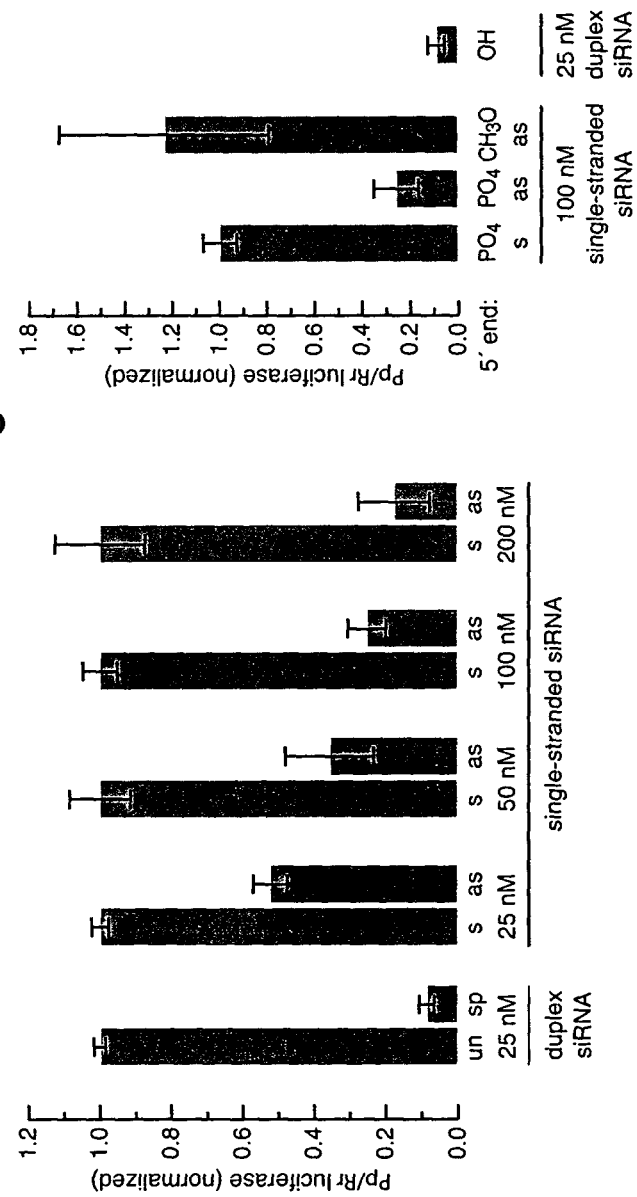

SEQUENCE LISTING

```
<160> NUMBER OF SEQ ID NOS: 24

<210> SEQ ID NO 1
<211> LENGTH: 21
<212> TYPE: RNA
<213> ORGANISM: Artificial Sequence
<220> FEATURE:
<223> OTHER INFORMATION: synthetic

<400> SEQUENCE: 1
ucgaaguauu ccgcguacgu g                                         21

<210> SEQ ID NO 2
<211> LENGTH: 21
<212> TYPE: RNA
<213> ORGANISM: Artificial Sequence
<220> FEATURE:
<223> OTHER INFORMATION: synthetic

<400> SEQUENCE: 2
cguacgcgga auacuucgau u                                         21

<210> SEQ ID NO 3
<211> LENGTH: 21
<212> TYPE: DNA
<213> ORGANISM: Artificial Sequence
<220> FEATURE:
<223> OTHER INFORMATION: synthetic combined DNA/RNA sequence
<220> FEATURE:
<221> NAME/KEY: misc_feature
<222> LOCATION: 1
<223> OTHER INFORMATION: n = methoxy deoxythymidine

<400> SEQUENCE: 3
ncgaaguauu ccgcguacgu g                                         21

<210> SEQ ID NO 4
<211> LENGTH: 21
<212> TYPE: RNA
<213> ORGANISM: Artificial Sequence
<220> FEATURE:
<223> OTHER INFORMATION: synthetic

<400> SEQUENCE: 4
cguacgcgga auacuucgau u                                         21
```

```
<210> SEQ ID NO 5
<211> LENGTH: 21
<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: 21
<223> OTHER INFORMATION: n = dideoxy cytosine

<400> SEQUENCE: 5
ucgaaguauu ccgcguacgu n                                              21

<210> SEQ ID NO 6
<211> LENGTH: 21
<212> TYPE: RNA
<213> ORGANISM: Artificial Sequence
<220> FEATURE:
<223> OTHER INFORMATION: synthetic

<400> SEQUENCE: 6
cguacgcgga auacuucgau u                                              21

<210> SEQ ID NO 7
<211> LENGTH: 21
<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: 21
<223> OTHER INFORMATION: n = amino modified guanine

<400> SEQUENCE: 7
ucgaaguauu ccgcguacgu n                                              21

<210> SEQ ID NO 8
<211> LENGTH: 21
<212> TYPE: RNA
<213> ORGANISM: Artificial Sequence
<220> FEATURE:
<223> OTHER INFORMATION: synthetic

<400> SEQUENCE: 8
cguacgcgga auacuucgau u                                              21

<210> SEQ ID NO 9
<211> LENGTH: 20
<212> TYPE: RNA
<213> ORGANISM: Artificial Sequence
<220> FEATURE:
<223> OTHER INFORMATION: synthetic

<400> SEQUENCE: 9
ucgaaguauu ccgcguacgu                                                20

<210> SEQ ID NO 10
<211> LENGTH: 21
<212> TYPE: RNA
<213> ORGANISM: Artificial Sequence
<220> FEATURE:
<223> OTHER INFORMATION: synthetic

<400> SEQUENCE: 10
cguacgcgga auacuucgau u                                              21
```

```
<210> SEQ ID NO 11
<211> LENGTH: 20
<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: 20
<223> OTHER INFORMATION: n = dideoxy cytosine

<400> SEQUENCE: 11
ucgaaguauu ccgcguacgn                                                    20

<210> SEQ ID NO 12
<211> LENGTH: 21
<212> TYPE: RNA
<213> ORGANISM: Artificial Sequence
<220> FEATURE:
<223> OTHER INFORMATION: synthetic

<400> SEQUENCE: 12
cguacgcgga auacuucgau u                                                  21

<210> SEQ ID NO 13
<211> LENGTH: 20
<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: 20
<223> OTHER INFORMATION: n = amino modified uracil

<400> SEQUENCE: 13
ucgaaguauu ccgcguacgn                                                    20

<210> SEQ ID NO 14
<211> LENGTH: 21
<212> TYPE: RNA
<213> ORGANISM: Artificial Sequence
<220> FEATURE:
<223> OTHER INFORMATION: synthetic

<400> SEQUENCE: 14
cguacgcgga auacuucgau u                                                  21

<210> SEQ ID NO 15
<211> LENGTH: 20
<212> TYPE: RNA
<213> ORGANISM: Artificial Sequence
<220> FEATURE:
<223> OTHER INFORMATION: synthetic

<400> SEQUENCE: 15
ucgaaguauu ccgcguacgc                                                    20

<210> SEQ ID NO 16
<211> LENGTH: 21
<212> TYPE: RNA
<213> ORGANISM: Artificial Sequence
<220> FEATURE:
<223> OTHER INFORMATION: synthetic

<400> SEQUENCE: 16
cguacgcgga auacuucgau u                                                  21
```

<210> SEQ ID NO 17
<211> LENGTH: 19
<212> TYPE: RNA
<213> ORGANISM: Artificial Sequence
<220> FEATURE:
<223> OTHER INFORMATION: synthetic

<400> SEQUENCE: 17
ucgaaguauu ccgcguacg                                                19

<210> SEQ ID NO 18
<211> LENGTH: 21
<212> TYPE: RNA
<213> ORGANISM: Artificial Sequence
<220> FEATURE:
<223> OTHER INFORMATION: synthetic

<400> SEQUENCE: 18
cguacgcgga auacuucgau u                                             21

<210> SEQ ID NO 19
<211> LENGTH: 19
<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: 19
<223> OTHER INFORMATION: n = amino modified guanine

<400> SEQUENCE: 19
ucgaaguauu ccgcguacn                                                19

<210> SEQ ID NO 20
<211> LENGTH: 21
<212> TYPE: RNA
<213> ORGANISM: Artificial Sequence
<220> FEATURE:
<223> OTHER INFORMATION: synthetic

<400> SEQUENCE: 20
cguacgcgga auacuucgau u                                             21

<210> SEQ ID NO 21
<211> LENGTH: 21
<212> TYPE: RNA
<213> ORGANISM: Artificial Sequence
<220> FEATURE:
<223> OTHER INFORMATION: synthetic

<400> SEQUENCE: 21
ugagguagua gguuguauag u                                             21

<210> SEQ ID NO 22
<211> LENGTH: 21
<212> TYPE: RNA
<213> ORGANISM: Artificial Sequence
<220> FEATURE:
<223> OTHER INFORMATION: synthetic

<400> SEQUENCE: 22
uauacaaccu acuaccucau u                                             21

<210> SEQ ID NO 23
<211> LENGTH: 21

```
<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: 1
<223> OTHER INFORMATION: n = deoxy thymidine
<220> FEATURE:
<221> NAME/KEY: misc_feature
<222> LOCATION: 21
<223> OTHER INFORMATION: n = amino modified uracil

<400> SEQUENCE: 23
ngagguagua gguuguauag n                                              21

<210> SEQ ID NO 24
<211> LENGTH: 21
<212> TYPE: RNA
<213> ORGANISM: Artificial Sequence
<220> FEATURE:
<223> OTHER INFORMATION: synthetic

<400> SEQUENCE: 24
uauacaaccu acuaccucau u                                              21
```

COMPOSITIONS FOR RNA INTERFERENCE AND METHODS OF USE THEREOF

RELATED APPLICATIONS

This application claims the benefit of copending U.S. provisional patent application Ser. No. 60/401,902 entitled "5' Phosphorylated, Single-Stranded siRNAs that Trigger RNA Interference", filed Aug. 7, 2002, and copending U.S. provisional patent application Ser. No. 60/408,786 entitled "Compositions for RNA interference and methods of use thereof", filed Sep. 5, 2002. The entire contents of the above-referenced applications are incorporated herein by this reference.

GOVERNMENT RIGHTS

This invention was made at least in part with government support under grant no. R01 GM62862-01 awarded by the National Institutes of Health. The government may have certain rights in this invention.

BACKGROUND OF THE INVENTION

In diverse eukaryotes, double-stranded RNA (dsRNA) triggers the destruction of mRNA sharing sequence with the double-strand (Hutvágner et al. (2002) *Curr. Opin. Genet. Dev.* 12:225-232; Hannon (2002) *Nature* 418:244-251). In animals and basal eukaryotes, this process is called RNA interference (RNAi) (Fire et al. (1998) *Nature* 391:806-811). There is now wide agreement that RNAi is initiated by the conversion of dsRNA into 21-23 nt fragments by the multidomain RNase III enzyme, Dicer (Bernstein et al. (2001) *Nature* 409:363-366; Billy et al. (2001) *Proc. Natl. Acad. Sci. USA* 98:14428-14433; Grishok et al. (2001) *Cell* 106:23-34; Ketting et al. (2001) *Genes Dev.* 15:2654-2659; Knight et al. (2001) *Science* 293:2269-2271; and Martens et al. (2002) *Cell* 13:445-453). These short RNAs are known as small interfering RNAs (siRNAs), and they direct the degradation of target RNAs complementary to the siRNA sequence (Zamore et al. (2000) *Cell* 101:25-33; Elbashir et al. (2001) *Nature* 411:494-498; Elbashir et al. (2001) *Genes Dev.* 15:188-200; Elbashir et al. (2001) *EMBO J.* 20:6877-6888; Nykänen et al. (2001) *Cell* 107:309-321; and Elbashir et al. (2002) *Clin. Pharmacol.* 26:199-213). In addition to its role in initiating RNAi, Dicer also cleaves ~70 nt precursor RNA stem-loop structures into single-stranded 21-23 nt RNAs known as microRNAs (miRNAs; Grishok et al. (supra); Hutvágner et al. (2001) *Science* 293:834-838; Ketting et al. (supra); and Reinhart et al. (2002) *Genes Dev.* 16:1616-1626). Like siRNAs, miRNAs bear 5' monophosphate and 3' hydroxyl groups, the signatures of RNase III cleavage products (Elbashir et al. (supra); Hutvágner et al. (supra). miRNAs are hypothesized to function in animals as translational repressors (Lee et al. (1993) *Cell* 75:843-854; Wightman et al. (1993) *Cell* 75:855-862; Ha et al. (1996) *Genes Dev.* 10:3041-3050; Moss et al. (1997) *Cell* 88:637-646; Olsen et al. (1999) *Dev. Biol.* 216:671-680; Reinhart et al. (2000) *Nature* 403:901-906; Zeng et al. (2002) *Molecular Cell* 9:1327-1333; and Seggerson et al. (2002) *Dev. Biol.* 243:215-225). The conversion of dsRNA into siRNAs requires additional protein co-factors that may recruit the dsRNA to Dicer or stabilize the siRNA products (Tabara et al. (1999) *Cell* 99:123-132; Grishok et al. (supra); Hammond et al. (2001) *Science* 293:1146-1150; and Tabara et al. (2002) *Cell* 109:861-871).

SUMMARY OF THE INVENTION

In *Drosophila*, several features of small interfering RNA (siRNA) structure are reported to be essential for RNA interference (RNAi). In particular, it is reported that siRNAs must be double stranded to be effective in mediating RNAi. Moreover, 5' phosphates and 3' hydroxyls are reported to be essential for RNA interference (RNAi). The present invention is based, at least in part, on the surprising discovery that single-stranded siRNAs are efficient in mediating target-specific RNAi. Moreover, in both *Drosophila* and mammalian cell extracts, as well as in vivo in human HeLa cells, a 5' phosphate is required for siRNA function. In contrast, there is no evidence in flies or humans for a role in RNAi for the siRNA 3' hydroxyl group. The present invention is further based, in part, on the premise that in both flies and mammals, each siRNA directs endonucleolytic cleavage of the target RNA at a single site. It can be concluded that the underlying mechanism of RNAi is conserved between flies and mammals and that RNA-dependent RNA polymerases are not required for RNAi in these organisms.

Accordingly, the present invention provides compositions for RNA interference and methods of use thereof. In particular, the invention provides single-stranded small interfering RNAs (ss-siRNAs) for mediating RNAi in vitro and in vivo. Methods for using said single-stranded small interfering RNAs are also provided. In particular, functional and genomic and proteomic methods are featured. Therapeutic methods are also featured.

The ss-siRNA molecules of the invention are particularly useful as reagents for RNA interference and have improved efficacy and are more economical to make than prior art siRNA agents.

Other features and advantages of the invention will be apparent from the following detailed description and claims.

BRIEF DESCRIPTION OF THE DRAWINGS

FIG. 2. RNAs used in this study. (A) *Photinus pyralis* (firefly) luciferase and let-7 siRNAs used in this study. The guide strand (antisense strand) is shown 5'-to-3' as the upper strand of each siRNA. Single-stranded siRNAs used in FIGS. 4, 5, and 6 correspond to the indicated guide strands. ddC, dideoxy Cytosine; AM, amino modifier. the first 10 siRNA duplexes correspond to the firefly luciferase sequence; the last two siRNA duplexes correspond to the let-7 sequence. (B) A schematic representation of the chimeric target RNA, indicating the relative positions of firefly luciferase sequences and sequences complementary to the let-7 miRNA found naturally in HeLa cells.

FIG. 7. A 5' phosphate, but not a 3' hydroxyl is required for siRNA duplexes to trigger RNAi in vivo in cultured human HeLa cells. (A) siRNA duplexes were examined for their ability to silence the *Photinus pyralis* (Pp; firefly) luciferase target reporter, relative to the *Renilla reniformis* (Rr) luciferase control reporter. ddC, 2',3' dideoxy C; AM, amino modifier. (B) Relative efficacy at limiting siRNA concentrations for siRNA duplexes with guide strands bearing either hydroxy (symbols connected by solid lines) or ddC (symbols connected by dashed line) 3' termini. Data are the average±standard deviation for three trials.

FIG. 8. Single-stranded siRNA triggers gene silencing in HeLa cells. (A) Single-stranded siRNA silencing as a function of siRNA concentration. (B) Blocking the 5' end of single-stranded siRNAs prevented their triggering target gene silencing. Gray bars indicate the average±standard deviation for three trials. Un, siRNA unrelated in sequence to the target RNA; sp, specific siRNA corresponding to the target RNA; s, sense strand; as, anti-sense strand.

DETAILED DESCRIPTION OF THE INVENTION

Figure 1:
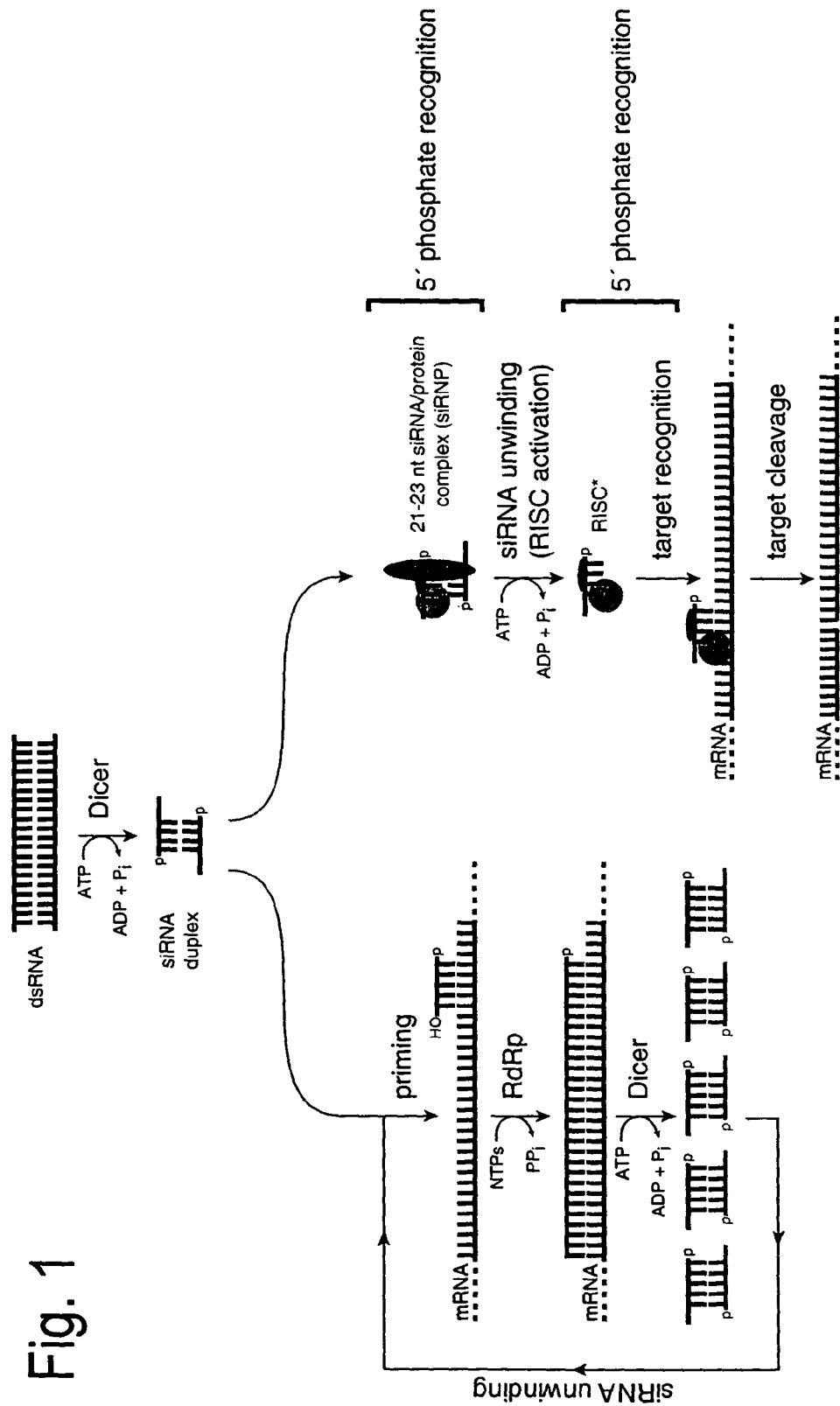
FIG. 1. Endonucleolytic cleavage model for RNAi in *Drosophila*. The model postulates that dsRNA is converted to siRNA by the ATP-dependent endoribonuclease Dicer, but the models differ as to the subsequent function of siRNAs. siRNAs are proposed to be incorporated into an endonuclease complex distinct from Dicer, the RISC. Assembly of the RISC is proposed to be ATP-dependent, whereas endonucleolytic cleavage of the target RNA is postulated to require no high energy cofactors.

In one aspect, the invention provides an isolated, single-stranded small interfering molecule (ss-siRNA), wherein the sequence of said ss-siRNA molecule is sufficiently complementary to a target mRNA sequence to direct target-specific RNA interference (RNAi) and wherein the 5' nucleotide is 5' phosphorylated or is capable of being 5' phosphorylated in situ or in vivo.

In one embodiment, the ss-siRNA is sufficiently complementary to a target mRNA, said target mRNA specifying the amino acid sequence of a cellular protein. In another embodiment, the ss-siRNA is sufficiently complementary to a target mRNA, said target mRNA specifying the amino acid sequence of a viral protein. Additionally or alternatively, the ss-siRNA can be modified such that the ss-siRNA has increased in situ or in vivo stability as compared to a corresponding unmodified ss-siRNA. Such a modified ss-siRNA can be modified by the substitution of at least one nucleotide with a modified nucleotide, which can be a sugar-modified nucleotide. The sugar-modified nucleotide can have a 2'-OH replaced by a moiety selected from the group consisting of H, OR, R, halo, SH, SR$^1$, NH$_2$, NHR, NR$_2$ and CN, wherein R is $C_1$-$C_6$ alkyl, alkenyl or alkynyl and halo is F, Cl, Br or I.

The sugar-modified nucleotide can be a 3' most nucleotide. In one embodiment, the 3' most nucleotide has a 2'-OH replaced by a moiety selected from the group consisting of H, OR, R, halo, SH, SR$^1$, NH$_2$, NHR, NR$_2$ and CN, wherein R is $C_1$-$C_6$ alkyl, alkenyl or alkynyl and halo is F, Cl, Br or I. In another embodiment, the 3' most nucleotide has a 3'-OH replaced by a moiety selected from the group consisting of H, OR, R, halo, SH, SR$^1$, NH$_2$, NHR, NR$_2$ and CN, wherein R is $C_1$-$C_6$ alkyl, alkenyl or alkynyl and halo is F, Cl, Br or I.

In yet another embodiment, the modified nucleotide is a backbone-modified nucleotide. In this embodiment, the backbone-modified nucleotide may contain a phosphorothioate group.

In yet another embodiment, the ss-siRNA of the invention can include between about 10 and 50 nucleotides, preferably between about 15 and 45 nucleotides, more preferably, between about 19 and 40 nucleotides.

In a further embodiment, the ss-siRNA of of the invention is chemically synthesized.

In another aspect, the invention provides a transgene that encodes any of the ss-siRNA described herein. In yet another aspect, the invention provides composition including an ss-siRNA molecule of the invention, and a pharmaceutically acceptable carrier.

In still yet another aspect, the invention provides a method of activating target-specific RNA interference (RNAi) in a cell. The method includes the step of introducing into said cell a single-stranded small interfering RNA molecule (ss-siRNA), wherein the sequence of said ss-siRNA molecule is sufficiently complementary to a target mRNA sequence to direct target-specific RNA interference (RNAi) and wherein the 5' nucleotide is 5' phosphorylated or is capable of being 5' phosphorylated in situ or in vivo, said ss-siRNA being introduced in an amount sufficient for degradation of the target mRNA to occur, thereby activating target-specific RNAi in the cell.

In one embodiment of this method, the ss-siRNA is introduced into the cell by contacting the cell with the ss-siRNA. In another, the ss-siRNA is introduced into the cell by contacting the cell with a composition comprising the ss-siRNA and a lipophillic carrier. In yet another, the ss-siRNA is introduced into the cell by transfecting or infecting the cell with a vector comprising nucleic acid sequences capable of producing the ss-siRNA when transcribed in situ. In yet another, the ss-siRNA is introduced into the cell by injecting into the cell a vector comprising nucleic acid sequences capable of producing the ss-siRNA when transcribed in situ. Such a vector includes transgene nucleic acid sequences in yet another embodiment of the invention.

In another embodiment of the method, the target mRNA specifies the amino acid sequence of a protein involved or predicted to be involved in a human disease or disorder.

In another aspect, the invention provides a cell obtained by a method of the invention. In various embodiments, the cell can be of mammalian origin, of murine origin, or of human origin. In another embodiment, cell is an embryonic stem cell. The invention further provides an organism derived from an embryonic stem cell obtained by a method of the invention.

In yet another aspect, the invention provides a method of activating target-specific RNA interference (RNAi) in an organism. The method includes the step of administering to said organism a single-stranded small interfering RNA molecule (ss-siRNA), wherein the sequence of said ss-siRNA molecule is sufficiently complementary to a target mRNA sequence to direct target-specific RNA interference (RNAi) and wherein the 5' nucleotide is 5' phosphorylated or is capable of being 5' phosphorylated in situ or in vivo, said ss-siRNA being administered in an amount sufficient for degradation of the target mRNA to occur, thereby activating target-specific RNAi in the organism.

In one embodiment, the the ss-siRNA is administered by an intravenous or intraperitoneal route. In another, the target mRNA specifies the amino acid sequence of a protein involved or predicted to be involved in a human disease or disorder.

The invention further provides an organism obtained by this method. In various embodiments, the organism can be of mammalian origin, murine origin or human origin. In any of these embodiments, a further embodiment may include organisms wherein the target mRNA specifies the amino acid sequence of a protein involved or predicted to be involved in a human disease or disorder. In a preferred embodiment, degradation of the target mRNA produces a loss-of-function phenotype.

In any of the methods of the invention, a further embodiment includes a method wherein degradation of the target mRNA is such that the protein specified by said target mRNA is decreased by at least 10%.

In yet another aspect, the invention provides a method of treating a disease or disorder associated with the activity of a protein specified by a target mRNA in a subject. The method includes administering to said subject a single-stranded small interfering RNA molecule (ss-siRNA), wherein the sequence of said ss-siRNA molecule is sufficiently complementary to the target mRNA sequence to direct target-specific RNA interference (RNAi) and wherein the 5' nucleotide is 5' phosphorylated or is capable of being 5' phosphorylated in situ or in vivo, said ss-siRNA being administered in an amount sufficient for degradation of the target mRNA to occur, thereby treating the disease or disorder associated with the protein.

In still yet another aspect, the invention provides a method for deriving information about the function of a gene in a cell or organism. The method includes the steps of: (a) introducing into said cell or organism a single-stranded small interfering RNA molecule (ss-siRNA), wherein the sequence of said ss-siRNA molecule is sufficiently complementary to a target mRNA sequence to direct target-specific RNA interference (RNAi) and wherein the 5' nucleotide is 5' phosphorylated or is capable of being 5' phosphorylated in situ or in vivo; (b) maintaining the cell or organism under conditions such that target-specific RNAi can occur; (c) determining a characteristic or property of said cell or organism; and (d) comparing said characteristic or property to a suitable control, the comparison yielding information about the function of the gene.

In yet another aspect, the invention provides a method of validating a candidate protein as a suitable target for drug discovery. The method includes the steps of: (a) introducing into a cell or organism a single-stranded small interfering RNA molecule (ss-siRNA), wherein the sequence of said ss-siRNA molecule is sufficiently complementary to a target mRNA sequence to direct target-specific RNA interference (RNAi) and wherein the 5' nucleotide is 5' phosphorylated or is capable of being 5' phosphorylated in situ or in vivo, said target mRNA specifying the amino acid sequence of the candidate protein; (b) maintaining the cell or organism under conditions such that target-specific RNAi can occur; (c) determining a characteristic or property of said cell or organism; and (d) comparing said characteristic or property to a suitable control, the comparison yielding information about whether the candidate protein is a suitable target for drug discovery.

In another aspect, the invention provides a kit comprising reagents for activating target-specific RNA interference (RNAi) in a cell or organism. The kit may include: (a) an isolated, single-stranded small interfering (ss-siRNA) molecule, wherein the sequence of said ss-siRNA molecule is sufficiently complementary to a target mRNA sequence to direct target-specific RNA interference (RNAi) and wherein the 5' nucleotide is 5' phosphorylated or is capable of being 5' phosphorylated in situ or in vivo; and (b) instructions for use.

So that the invention may be more readily understood, certain terms are first defined.

The term "nucleoside" refers to a molecule having a purine or pyrimidine base covalently linked to a ribose or deoxyribose sugar. Exemplary nucleosides include adenosine, guanosine, cytidine, uridine and thymidine. The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester linkage between 5' and 3' carbon atoms.

The term "RNA" or "RNA molecule" or "ribonucleic acid molecule" refers to a polymer of ribonucleotides. The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference.

The term "nucleotide analog" or "altered nucleotide" or "modified nucleotide" refers to a non-standard nucleotide, including non-naturally occurring ribonucleotides or deoxyribonucleotides. Preferred nucleotide analogs are modified at any position so as to alter certain chemical properties of the nucleotide yet retain the ability of the nucleotide analog to perform its intended function. Examples of positions of the nucleotide which may be derivitized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, *Antisense Nucleic Acid Drug Dev.*, 2000 Aug. 10(4):297-310.

Nucleotide analogs may also comprise modifications to the sugar portion of the nucleotides. For example the 2' OH-group may be replaced by a group selected from H, OR, R, F, Cl, Br, I, SH, SR, $NH_2$, NHR, $NR_2$, COOR, or OR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, *Antisense Nucleic Acid Drug Dev.* 2000 Apr. 10(2):117-21, Rusckowski et al. *Antisense Nucleic Acid Drug Dev.* 2000 Oct. 10(5):333-45, Stein, *Antisense Nucleic Acid Drug Dev.* 2001 Oct. 11(5): 317-25, Vorobjev et al. *Antisense Nucleic Acid Drug Dev.* 2001 Apr. 11(2):77-85, and U.S. Pat. No. 5,684,143. Certain of the above-referenced modifications (e.g., phosphate group modifications) preferably decrease the rate of hydrolysis of, for example, polynucleotides comprising said analogs in vivo or in vitro.

The term "oligonucleotide" refers to a short polymer of nucleotides and/or nucleotide analogs. The term "RNA analog" refers to an polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. As discussed above, the oligonucleotides may be linked with linkages which result in a lower rate of hydrolysis of the RNA analog as compared to an RNA molecule with phosphodiester linkages. For example, the nucleotides of the analog may comprise methylenediol, ethylene diol, oxymethylthio, oxyethylthio, oxycarbonyloxy, phosphorodiamidate, phophoroamidate, and/or phosphorothioate linkages. Preferred RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA interference.

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of target genes.

A ss-siRNA having a "sequence sufficiently complementary to a target mRNA sequence to direct target-specific RNA interference (RNAi)" means that the ss-siRNA has a sequence sufficient to trigger the destruction of the target mRNA by the RNAi machinery or process.

The term "phosphorylated" means that at least one phosphate group is attached to a chemical (e.g., organic) compound. Phosphate groups can be attached, for example, to proteins or to sugar moieties via the following reaction: free hydroxyl group+phosphate donor→phosphate ester linkage. The term "5' phosphorylated" is used to describe, for example, polynucleotides or oligonucleotides having a phosphate group attached via ester linkage to the C5 hydroxyl of the 5' sugar (e.g., the 5' ribose or deoxyribose, or an analog of same). Mono-, di-, and triphosphates are common. Also intended to be included within the scope of the instant invention are phosphate group analogs which function in the same or similar manner as the mono-, di-, or triphosphate groups found in nature (see e.g., exemplified analogs.)

As used herein, the term "isolated RNA" (e.g., "isolated ssRNA", "isolated siRNA" or "isolated ss-siRNA") refers to RNA molecules which are substantially free of other cellular material, or culture medium when produced by recombinant techniques, or substantially free of chemical precursors or other chemicals when chemically synthesized.

The term "in vitro" has its art recognized meaning, e.g., involving purified reagents or extracts, e.g., cell extracts. The term "in vivo" alos has its art recognized meaning, e.g., involving living cells, e.g., immortalized cells, primary cells, cell lines, and/or cells in an organism.

A gene "involved" in a disorder includes a gene, the normal or aberrant expression or function of which effects or causes a disease or disorder or at least one symptom of said disease or disorder The phrase "examining the function of a gene in a cell or organism" refers to examining or studying the expression, activity, function or phenotype arising therefrom.

Various methodologies of the instant invention include step that involves comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing a ss-siRNA of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Various aspects of the invention are described in further detail in the following subsections.

I. RNA Molecules

The present invention features "single-stranded small interfering RNA molecules" ("ss-siRNA molecules" or "ss-siRNA"), methods of making said ss-siRNA molecules and methods (e.g., research and/or therapeutic methods) for using said ss-siRNA molecules. Preferably, the ss-siRNA molecule has a length from about 10-50 or more nucleotides. More preferably, the ss-siRNA molecule has a length from about 15-45 nucleotides. Even more preferably, the ss-siRNA molecule has a length from about 19-40 nucleotides. The ss-siRNA molecules of the invention further have a sequence that is "sufficiently complementary" to a target mRNA sequence to direct target-specific RNA interference (RNAi), as defined herein, i.e., the ss-siRNA has a sequence sufficient to trigger the destruction of the target mRNA by the RNAi machinery or process. The ss-siRNA molecule can be designed such that every residue is complementary to a residue in the target molecule. Alternatively, substitutions can be made within the molecule to increase stability and/or enhance processing activity of said molecule. Substitutions can be made within the strand or can be made to residues a the ends of the strand. The 5'-terminus is, most preferably, phosphorylated (i.e., comprises a phosphate, diphosphate, or triphosphate group). Contrary to previous findings, however, that the 3' end of an siRNA be a hydroxyl group in order to facilitate RNAi, the present inventors have demonstrated that there is no requirement for a 3' hydroxyl group when the active agent is a ss-siRNA molecule. Accordingly, the invention features, in particular, ss-siRNA molecules wherein the 3' end (i.e., C3 of the 3' sugar) lacks a hydroxyl group (i.e., ss-siRNA molecules lacking a 3' hydroxyl or C3 hydroxyl on the 3' sugar (e.g., ribose or deoxyribose).

The target RNA cleavage reaction guided by siRNAs (e.g., by ss-siRNAs) is highly sequence specific. In general, siRNA containing a nucleotide sequences identical to a portion of the target gene are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition.

Moreover, not all positions of a siRNA contribute equally to target recognition. Mismatches in the center of the siRNA are most critical and essentially abolish target RNA cleavage. In contrast, the 3' nucleotides of the siRNA do not contribute significantly to specificity of the target recognition. In particular, residues 3' of the siRNA sequence which is complementary to the target RNA (e.g., the guide sequence) are not critical for target RNA cleavage.

Sequence identity may determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) *Proc. Natl. Acad. Sci. USA* 87:2264-68, modified as in Karlin and Altschul (1993) *Proc. Natl. Acad. Sci. USA* 90:5873-77. Such an algorithm is incorporated into the BLAST programs (version 2.0) of Altschul, et al. (1990) *J. Mol. Biol.* 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) *Nucleic Acids Res*. 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, *CABIOS* (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

Greater than 90% sequence identity, e.g., 91%, 92%, 93%, 94%, 95%, 96%, 97%, 98%, 99% or even 100% sequence identity, between the ss-siRNA and the portion of the target gene is preferred. Alternatively, the ss-siRNA may be defined functionally as a nucleotide sequence (or oligonucleotide sequence) that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing). Additional preferred hybridization conditions include hybridization at 70° C. in 1×SSC or 50° C. in 1×SSC, 50% formamide followed by washing at 70° C in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6(log10[Na+])+0.41(% G+C)−(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, *Molecular Cloning: A Laboratory Manual*, Cold Spring Harbor Laboratory Press, Cold Spring Harbor, N.Y., chapters 9 and 11, and *Current Protocols in Molecular Biology*, 1995, F. M. Ausubel et al., eds., John Wiley & Sons, Inc., sections 2.10 and 6.3-6.4, incorporated herein by reference. The length of the identical nucleotide sequences may be at least about 10, 12, 15, 17, 20, 22, 25, 27, 30, 32, 35, 37, 40, 42, 45, 47 or 50 bases.

In a preferred aspect, the RNA molecules of the present invention are modified to improve stability in serum or in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference. For example, the absence of a 2' hydroxyl may significantly enhance the nuclease resistance of the ss-siRNAs in tissue culture medium.

In an especially preferred embodiment of the present invention the RNA molecule may contain at least one modified nucleotide analogue. The nucleotide analogues may be located at positions where the target-specific activity, e.g., the RNAi mediating activity is not substantially effected, e.g., in a region at the 5'-end and/or the 3'-end of the RNA molecule. Particularly, the ends may be stabilized by incorporating modified nucleotide analogues.

Preferred nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In preferred backbone-modified ribonucleotides the phosphoester group connecting to adjacent ribonucleotides is replaced by a modified group, e.g., of phosphothioate group. In preferred sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

Also preferred are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

RNA may be produced enzymatically or by partial/total organic synthesis, any modified nibonucleotide can be introduced by in vitro enzymatic or organic synthesis. In one embodiment, a ss-siRNA is prepared chemically. Methods of synthesizing RNA molecules are known in the art, in particular, the chemical synthesis methods as de scribed in Verma and Eckstein (1998) *Annul Rev. Biochem.* 67:99-134. In another embodiment, a ss-siRNA is prepared enzymatically. For example, a ds-siRNA can be prepared by enzymatic processing of a long ds RNA having sufficient complementarity to the desired target mRNA. Processing of long ds RNA can be accomplished in vitro, for example, using appropriate cellular lysates and ds-siRNAs can be subsequently purified by gel electrophoresis or gel filtration. ds-siRNA can then be denatured according to art-recognized methodologies. In an exemplary embodiment, RNA can be purified from a mixture by extraction with a solvent or resin, precipitation, electrophoresis, chromatography, or a combination thereof. Alternatively, the RNA may be used with no or a minimum of purification to avoid losses due to sample processing. Alternatively, the single-stranded RNAs can also be prepared by enzymatic transcription from synthetic DNA templates or from DNA plasmids isolated from recombinant bacteria. Typically, phage RNA polymerases are used such as T7, T3 or SP6 RNA polymerase (Milligan and Uhlenbeck (1989) *Methods Enzymol*. 180:51-62). The RNA may be dried for storage or dissolved in an aqueous solution. The solution may contain buffers or salts to inhibit annealing, and/or promote stabilization of the single strands.

In one embodiment, the target mRNA of the invention specifies the amino acid sequence of a cellular protein (e.g., a nuclear, cytoplasmic, transmembrane, or membrane-associated protein). In another embodiment, the target mRNA of the invention specifies the amino acid sequence of an extracellular protein (e.g., an extracellular matrix protein or secreted protein). As used herein, the phrase "specifies the amino acid sequence" of a protein means that the mRNA sequence is translated into the amino acid sequence according to the rules of the genetic code. The following classes of proteins are listed for illustrative purposes: developmental proteins (e.g., adhesion molecules, cyclin kinase inhibitors, Wnt family members, Pax family members, Winged helix family members, Hox family members, cytokines/lymphokines and their receptors, growth/differentiation factors and their receptors, neurotransmitters and their receptors); oncogene-encoded proteins (e.g., ABLI, BCLI, BCL2, BCL6, CBFA2, CBL, CSFIR, ERBA, ERBB, EBRB2, ETSI, ETSI, ETV6, FGR, FOS, FYN, HCR, HRAS, JUN, KRAS, LCK, LYN, MDM2, MLL, MYB, MYC, MYCLI, MYCN, NRAS, PIM I, PML, RET, SRC, TALI, TCL3, and YES); tumor suppressor proteins (e.g., APC, BRCA1, BRCA2, MADH4, MCC, NF I, NF2, RB I, TP53, and WTI); and enzymes (e.g., ACC synthases and oxidases, ACP desaturases and hydroxylases, ADP-glucose pyrophorylases, ATPases, alcohol dehydrogenases, amylases, amyloglucosidases, catalases, cellulases, chalcone synthases, chitinases, cyclooxygenases, decarboxylases, dextriinases, DNA and RNA polymerases, galactosidases, glucanases, glucose oxidases, granule-bound starch synthases, GTPases, helicases, hernicellulases, integrases, inulinases, invertases, isomerases, kinases, lactases, lipases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases, and xylanases).

In a preferred aspect of the invention, the target mRNA molecule of the invention specifies the amino acid sequence of a protein associated with a pathological condition. For example, the protein may be a pathogen-associated protein (e.g., a viral protein involved in immunosuppression of the host, replication of the pathogen, transmission of the pathogen, or maintenance of the infection), or a host protein which facilitates entry of the pathogen into the host, drug metabolism by the pathogen or host, replication or integration of the pathogen's genome, establishment or spread of infection in the host, or assembly of the next generation of pathogen. Alternatively, the protein may be a tumor-associated protein or an autoimmune disease-associated protein.

In one embodiment, the target mRNA molecule of the invention specifies the amino acid sequence of an endogenous protein (i.e., a protein present in the genome of a cell or organism). In another embodiment, the target mRNA molecule of the invention specified the amino acid sequence of a heterologous protein expressed in a recombinant cell or a genetically altered organism. In another embodiment, the target mRNA molecule of the invention specified the amino acid sequence of a protein encoded by a transgene (i.e., a gene construct inserted at an ectopic site in the genome of the cell). In yet another embodiment, the target mRNA molecule of the invention specifies the amino acid sequence of a protein encoded by a pathogen genome which is capable of infecting a cell or an organism from which the cell is derived.

By inhibiting the expression of such proteins, valuable information regarding the function of said proteins and therapeutic benefits which may be obtained from said inhibition may be obtained.

In one embodiment, ss-siRNAs are synthesized either in vivo, in situ, or in vitro. Endogenous RNA polymerase of the cell may mediate transcription in vivo or in situ, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the ss-siRNA. Inhibition may be targeted by specific transcription in an organ, tissue, or cell type; stimulation of an environmental condition (e.g., infection, stress, temperature, chemical inducers); and/or engineering transcription at a developmental stage or age. A transgenic organism that expresses ss-siRNA from a recombinant construct may be produced by introducing the construct into a zygote, an embryonic stem cell, or another multipotent cell derived from the appropriate organism.

II. Methods of Introducing RNAs, Vectors, and Host Cells

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus the RNA may be introduced along with components that perform one or more of the following activities: enhance RNA uptake by the cell, inhibit annealing of single strands, stabilize the single strands, or other-wise increase inhibition of the target gene.

RNA may be directly introduced into the cell (i.e., intracellularly); or introduced extracellularly into a cavity, interstitial space, into the circulation of an organism, introduced orally, or may be introduced by bathing a cell or organism in a solution containing the RNA. Vascular or extravascular circulation, the blood or lymph system, and the cerebrospinal fluid are sites where the RNA may be introduced.

The cell with the target gene may be derived from or contained in any organism. The organism may a plant, animal, protozoan, bacterium, virus, or fungus. The plant may be a monocot, dicot or gymnosperm; the animal may be a vertebrate or invertebrate. Preferred microbes are those used in agriculture or by industry, and those that are pathogenic for plants or animals. Fungi include organisms in both the mold and yeast morphologies. Plants include arabidopsis; field crops (e.g., alfalfa, barley, bean, com, cotton, flax, pea, rape, nice, rye, safflower, sorghum, soybean, sunflower, tobacco, and wheat); vegetable crops (e.g., asparagus, beet, broccoli, cabbage, carrot, cauliflower, celery, cucumber, eggplant, lettuce, onion, pepper, potato, pumpkin, radish, spinach, squash, taro, tomato, and zucchini); fruit and nut crops (e.g., almond, apple, apricot, banana, black-berry, blueberry, cacao, cherry, coconut, cranberry, date, faJoa, filbert, grape, grapefr-uit, guava, kiwi, lemon, lime, mango, melon, nectarine, orange, papaya, passion fruit, peach, peanut, pear, pineapple, pistachio, plum, raspberry, strawberry, tangerine, walnut, and watermelon); and ornamentals (e.g., alder, ash, aspen, azalea, birch, boxwood, camellia, carnation, chrysanthemum, elm, fir, ivy, jasmine, juniper, oak, palm, poplar, pine, redwood, rhododendron, rose, and rubber). Examples of vertebrate animals include fish, mammal, cattle, goat, pig, sheep, rodent, hamster, mouse, rat, primate, and human; invertebrate animals include nematodes, other worms, drosophila, and other insects.

The cell having the target gene may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

Depending on the particular target gene and the dose of double stranded RNA material delivered, this process may provide partial or complete loss of function for the target gene. A reduction or loss of gene expression in at least 50%, 60%, 70%, 80%, 90%, 95% or 99% or more of targeted cells is exemplary. Inhibition of gene expression refers to the absence (or observable decrease) in the level of protein and/or mRNA product from a target gene. Specificity refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS).

For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentarnycin, hygromycin, kanamycin, lincomycin, methotrexate, phosphinothricin, puromycin, and tetracyclin. Depending on the assay, quantitation of the amount of gene expression allows one to determine a degree of inhibition which is greater than 10%, 33%, 50%, 90%, 95% or 99% as compared to a cell not treated according to the present invention. Lower doses of injected material and longer times after administration of ss-siRNA may result in inhibition in a smaller fraction of cells (e.g., at least 10%, 20%, 50%, 75%, 90%, or 95% of targeted cells). Quantitation of gene expression in a cell may show similar amounts of inhibition at the level of accumulation of target mRNA or translation of target protein. As an example, the efficiency of inhibition may be determined by assessing the amount of gene product in the cell; mRNA may be detected with a hybridization probe having a nucleotide sequence outside the region used for the inhibitory double-stranded RNA, or translated polypeptide may be detected with an antibody raised against the polypeptide sequence of that region.

The RNA may be introduced in an amount which allows delivery of at least one copy per cell. Higher doses (e.g., at least 5, 10, 100, 500 or 1000 copies per cell) of material may yield more effective inhibition; lower doses may also be useful for specific applications.

III. Methods of Treatment:

The present invention provides for both prophylactic and therapeutic methods of treating a subject at risk of (or susceptible to) a disorder or having a disorder associated with aberrant or unwanted target gene expression or activity. "Treatment", or "treating" as used herein, is defined as the application or administration of a therapeutic agent (e.g., a ss-siRNA or vector or transgene encoding same) to a patient, or application or administration of a therapeutic agent to an isolated tissue or cell line from a patient, who has a disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the target gene molecules of the present invention or target gene modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant or unwanted target gene expression or activity, by administering to the subject a therapeutic agent (e.g., a ss-siRNA or vector or transgene encoding same). Subjects at risk for a disease which is caused or contributed to by aberrant or unwanted target gene expression or activity can be identified by, for example, any or a combination of diagnostic or prognostic assays as described herein. Administration of a prophylactic agent can occur prior to the manifestation of symptoms characteristic of the target gene aberrancy, such that a disease or disorder is prevented or, alternatively, delayed in its progression. Depending on the type of target gene aberrancy, for example, a target gene, target gene agonist or target gene antagonist agent can be used for treating the subject. The appropriate agent can be determined based on screening assays described herein.

2. Therapeutic Methods

Another aspect of the invention pertains to methods of modulating target gene expression, protein expression or activity for therapeutic purposes. Accordingly, in an exemplary embodiment, the modulatory method of the invention involves contacting a cell capable of expressing target gene with a therapeutic agent (e.g., a ss-siRNA or vector or transgene encoding same) that is specific for the target gene or protein (e.g., is specific for the mRNA encoded by said gene or specifying the amino acid sequence of said protein) such that expression or one or more of the activities of target protein is modulated. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a target gene polypeptide or nucleic acid molecule. Inhibition of target gene activity is desirable in situations in which target gene is abnormally unregulated and/or in which decreased target gene activity is likely to have a beneficial effect.

3. Pharmacogenomics

The therapeutic agents (e.g., a ss-siRNA or vector or transgene encoding same) of the invention can be administered to individuals to treat (prophylactically or therapeutically) disorders associated with aberrant or unwanted target gene activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a therapeutic agent as well as tailoring the dosage and/or therapeutic regimen of treatment with a therapeutic agent.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10-11): 983-985 and Linder, M. W. et al. (1997) *Clin. Chem.* 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a target gene polypeptide of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a therapeutic agent of the present invention can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a therapeutic agent, as described herein.

Therapeutic agents can be tested in an appropriate animal model. For example, an ss-siRNA (or expression vector or transgene encoding same) as described herein can be used in an animal model to determine the efficacy, toxicity, or side effects of treatment with said agent. Alternatively, a therapeutic agent can be used in an animal model to determine the mechanism of action of such an agent. For example, an agent can be used in an animal model to determine the efficacy, toxicity, or side effects of treatment with such an agent. Alternatively, an agent can be used in an animal model to determine the mechanism of action of such an agent.

IV. Pharmaceutical Compositions

The invention pertains to uses of the above-described agents for therapeutic treatments as described infra. Accordingly, the modulators of the present invention can be incorporated into pharmaceutical compositions suitable for administration. Such compositions typically comprise the nucleic acid molecule, protein, antibody, or modulatory compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, intraperitoneal, intramuscular, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions for administration.

V. Knockout and/or Knockdown Cells or Organisms

A further preferred use for the ss-siRNA molecules of the present invention (or vectors or transgenes encoding same) is a functional analysis to be carried out in eukaryotic cells, or eukaryotic non-human organisms, preferably mammalian cells or organisms and most preferably human cells, e.g. cell lines such as HeLa or 293 or rodents, e.g. rats and mice. By administering a suitable ss-siRNA molecules which is sufficiently complementary to a target mRNA sequence to direct target-specific RNA interference, a specific knockout or knockdown phenotype can be obtained in a target cell, e.g. in cell culture or in a target organism.

Thus, a further subject matter of the invention is a eukaryotic cell or a eukaryotic non-human organism exhibiting a target gene-specific knockout or knockdown phenotype comprising a fully or at least partially deficient expression of at least one endogeneous target gene wherein said cell or organism is transfected with at least one vector comprising DNA encoding a ss-siRNA molecule capable of inhibiting the expression of the target gene. It should be noted that the present invention allows a target-specific knockout or knockdown of several different endogeneous genes due to the specificity of the ss-siRNAi.

Gene-specific knockout or knockdown phenotypes of cells or non-human organisms, particularly of human cells or non-human mammals may be used in analytic to procedures, e.g. in the functional and/or phenotypical analysis of complex physiological processes such as analysis of gene expression profiles and/or proteomes. Preferably the analysis is carried out by high throughput methods using oligonucleotide based chips.

Using RNAi based knockout or knockdown technologies, the expression of an endogeneous target gene may be inhibited in a target cell or a target organism. The endogeneous gene may be complemented by an exogeneous target nucleic acid coding for the target protein or a variant or mutated form of the target protein, e.g. a gene or a DNA, which may optionally be fused to a further nucleic acid sequence encoding a detectable peptide or polypeptide, e.g. an affinity tag, particularly a multiple affinity tag.

Variants or mutated forms of the target gene differ from the endogeneous target gene in that they encode a gene product which differs from the endogeneous gene product on the amino acid level by substitutions, insertions and/or deletions of single or multiple amino acids. The variants or mutated forms may have the same biological activity as the endogeneous target gene. On the other hand, the variant or mutated target gene may also have a biological activity, which differs from the biological activity of the endogeneous target gene, e.g., a partially deleted activity, a completely deleted activity, an enhanced activity etc. The complementation may be accomplished by compressing the polypeptide encoded by the endogeneous nucleic acid, e.g. a fusion protein comprising the target protein and the affinity tag and the double stranded RNA molecule for knocking out the endogeneous gene in the target cell. This compression may be accomplished by using a suitable expression vector expressing both the polypeptide encoded by the endogenous nucleic acid, e.g. the tag-modified target protein and the double stranded RNA molecule or alternatively by using a combination of expression vectors. Proteins and protein complexes which are synthesized de novo in the target cell will contain the exogenous gene product, e.g., the modified fusion protein. In order to avoid suppression of the exogenous gene product by the ss-siRNAi molecule, the nucleotide sequence encoding the exogenous nucleic acid may be altered at the DNA level (with or without causing mutations on the amino acid level) in the part of the sequence which so is homologous to the ss-siRNA molecule. Alternatively, the endogeneous target gene may be complemented by corresponding nucleotide sequences from other species, e.g. from mouse.

VI. Functional Genomics and/or Proteomics

Preferred applications for the cell or organism of the invention is the analysis of gene expression profiles and/or proteomes. In an especially preferred embodiment an analysis of a variant or mutant form of one or several target proteins is carried out, wherein said variant or mutant forms are reintroduced into the cell or organism by an exogenous target nucleic acid as described above. The combination of knockout of an endogeneous gene and rescue by using mutated, e.g partially deleted exogenous target has advantages compared to the use of a knockout cell. Further, this method is particularly suitable for identifying functional domains of the targeted protein. In a further preferred embodiment a comparison, e.g of gene expression profiles and/or proteomes and/or phenotypic characteristics of at least two cells or organisms is carried out. These organisms are selected from: (i) a control cell or control organism without target gene inhibition, (ii) a cell or organism with target gene inhibition and (iii) a cell or organism with target gene inhibition plus target gene complementation by an exogenous target nucleic acid.

Furthermore, the RNA knockout complementation method may be used for is preparative purposes, e.g. for the affinity purification of proteins or protein complexes from eukaryotic cells, particularly mammalian cells and more particularly human cells. In this embodiment of the invention, the exogenous target nucleic acid preferably codes for a target protein which is fused to art affinity tag. This method is suitable for functional proteome analysis in mammalian cells, particularly human cells.

Another utility of the present invention could be a method of identifying gene function in an organism comprising the use of ss-siRNA to inhibit the activity of a target gene of previously unknown function. Instead of the time consuming and laborious isolation of mutants by traditional genetic screening, functional genomics would envision determining the function of uncharacterized genes by employing the invention to reduce the amount and/or alter the timing of target gene activity. The invention could be used in determining potential targets for pharmaceutics, understanding normal and pathological events associated with development, determining signaling pathways responsible for postnatal development/aging, and the like. The increasing speed of acquiring nucleotide sequence information from genomic and expressed gene sources, including total sequences for the yeast, *D. melanogaster*, and *C. elegans* genomes, can be coupled with the invention to determine gene function in an organism (e.g., nematode). The preference of different organisms to use particular codons, searching sequence databases for related gene products, correlating the linkage map of genetic traits with the physical map from which the nucleotide sequences are derived, and artificial intelligence methods may be used to define putative open reading frames from the nucleotide sequences acquired in such sequencing projects. A simple assay would be to inhibit gene expression according to the partial sequence available from an expressed sequence tag (EST). Functional alterations in growth, development, metabolism, disease resistance, or other biological processes would be indicative of the normal role of the EST's gene product.

The ease with which RNA can be introduced into an intact cell/organism containing the target gene allows the present invention to be used in high throughput screening (HTS). Solutions containing ss-siRNAs that are capable of inhibiting the different expressed genes can be placed into individual wells positioned on a microtiter plate as an ordered array, and intact cells/organisms in each well can be assayed for any changes or modifications in behavior or development due to inhibition of target gene activity. The amplified RNA can be fed directly to, injected into, the cell/organism containing the target gene. Alternatively, the ss-siRNA can be produced from a vector, as described herein. Vectors can be injected into, the cell/organism containing the target gene. The function of the target gene can be assayed from the effects it has on the cell/organism when gene activity is inhibited. This screening could be amenable to small subjects that can be processed in large number, for example: arabidopsis, bacteria, drosophila, fungi, nematodes, viruses, zebrafish, and tissue culture cells derived from mammals. A nematode or other organism that produces a colorimetric, fluorogenic, or luminescent signal in response to a regulated promoter (e.g., transfected with a reporter gene construct) can be assayed in an HTS format.

The present invention may be useful in allowing the inhibition of essential genes. Such genes may be required for cell or organism viability at only particular stages of development or cellular compartments. The functional equivalent of conditional mutations may be produced by inhibiting activity of the target gene when or where it is not required for viability. The invention allows addition of ss-siRNA at specific times of development and locations in the organism without introducing permanent mutations into the target genome.

VII. Screening Assays

The methods of the invention are also suitable for use in methods to identify and/or characterize potential pharmacological agents, e.g. identifying new pharmacological agents from a collection of test substances and/or characterizing mechanisms of action and/or side effects of known pharmacological agents.

Thus, the present invention also relates to a system for identifying and/or characterizing pharmacological agents acting on at least one target protein comprising: (a) a eukaryotic cell or a eukaryotic non-human organism capable of expressing at least one endogenous target gene coding for said so target protein, (b) at least one ss-siRNA molecule capable of inhibiting the expression of said at least one endogeneous target gene, and (c) a test substance or a collection of test substances wherein pharmacological properties of said test substance or said collection are to be identified and/or characterized. Further, the system as described above preferably comprises: (d) at least one exogenous target nucleic acid coding for the target protein or a variant or mutated form of the target protein wherein said exogenous target nucleic acid differs from the endogeneous target gene on the nucleic acid level such that the expression of the exogenous target nucleic acid is substantially less inhibited by the ss-siRNA molecule than the expression of the endogeneous target gene.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); (Ladner supra.)).

In a preferred embodiment, the library is a natural product library, e.g., a library produced by a bacterial, fungal, or yeast culture. In another preferred embodiment, the library is a synthetic compound library.

This invention is further illustrated by the following examples which should not be construed as limiting. The contents of all references, patents and published patent applications cited throughout this application are incorporated herein by reference.

EXAMPLES

Overview of Examples I-II

How siRNAs direct target cleavage and whether a single mechanism explains the function of siRNAs in post-transcriptional gene silencing in plants, quelling in fungi, and RNAi in animals remain unknown. Furthermore, how siRNAs are permitted to enter the RNAi pathway while other 21-23 nt RNAs seem to be excluded cannot yet be fully explained.

Three models have been proposed for RNAi in *Drosophila*. Each model seeks to explain the mechanism by which siRNAs direct target RNA destruction. In one model target destruction requires an RNA-dependent RNA polymerase (RdRP) to convert the target mRNA into dsRNA (Lipardi et al. (2001) *Cell* 107:297-301). The RdRP is hypothesized to use single-stranded siRNAs as primers for the target RNA-templated synthesis of complementary RNA (cRNA). The resulting cRNA/target RNA hybrid is proposed to then be cleaved by Dicer, destroying the mRNA and generating new siRNAs in the process. Key features of this model are that the ATP-dependent, dsRNA-specific endonuclease Dicer acts twice in the RNAi pathway, that target destruction should require nucleotide triphosphates to support the production of cRNA, and that a 3' hydroxyl group is essential for siRNA function, since siRNAs are proposed to serve as primers for new RNA synthesis.

A second model proposes that single-stranded siRNAs do not act as primers for an RdRP, but instead assemble along the length of the target RNA and are then ligated together by an RNA ligase to generate cRNA (Lipardi et al. (supra); Nishikura (2001) *Cell* 107:415-418). The cRNA/target RNA hybrid would then be destroyed by Dicer. This model predicts that target recognition and destruction should require ATP (or perhaps an NAD-derived high energy cofactor) to catalyze ligation, as well as ATP to support Dicer cleavage. Like the first model, the ligation hypothesis predicts that an siRNA 3' hydroxyl group will be absolutely required for RNAi. Furthermore, a 5' phosphate should be required for siRNA ligation. Unlike the first model, however, ribonucleotide triphosphates other than ATP should not be required for target destruction.

A third model (FIG. 1) hypothesizes that two distinct enzymes or enzyme complexes act in the RNAi pathway (Hammond et al. (2000) *Nature* 404:293-296; Zamore et al. (supra); and Nykänen et al. (supra)). As in the first model, Dicer is proposed to generate siRNAs from dsRNA. These siRNAs are then incorporated into a second enzyme complex, the RNA-induced silencing complex (RISC), in an ATP-dependent step or series of steps during which the siRNA duplex is unwound into single strands. The resulting single-stranded siRNA is proposed to guide the RISC to recognize and cleave the target RNA in a step or series of steps requiring no nucleotide cofactors whatsoever. The absence of a nucleotide triphosphate requirement for target recognition and cleavage is a key feature of this model.

The present inventors have previously demonstrated by two different experimental protocols that both recognition and endonucleolytic cleavage of a target RNA proceeds efficiently in the presence of less than 50 nM ATP, a concentration presumed to be insufficient to support either the synthesis of new RNA or the ligation of multiple siRNAs into cRNA (Nykänen et al. (supra)). However, these data also revealed an absolute requirement for a 5' phosphate for siRNAs to direct RNAi in *Drosophila* embryo lysates, a finding that was interpreted to reflect an authentication step in the assembly of the RNAi-enzyme complex, the RISC. It was envisioned that the 5' phosphate was involved in obligatory non-covalent interactions with one or more protein components of the RNAi pathway. Nonetheless, the 5' phosphate requirement might formally reflect a requirement for the phosphate group in covalent interactions, such as the ligation of multiple siRNAs to generate cRNA (Nishikura (2001) *Cell* 107:415-418).

To distinguish among these three models, the requirement for a 5' phosphate and a 3' hydroxyl group on the anti-sense strand of the siRNA duplex was examined. First, the role of these functional groups in RNAi using both *Drosophila* embryo lysates and human HeLa S100 extract was examined. Human HeLa S100 extract, like *Drosophila* embryo lysates, supports RNAi in vitro. Second, the findings were validated in vivo in human HeLa cells. The data support a model for the RNAi pathway in which siRNAs function as guides for an endonuclease complex that mediates target RNA destruction. The data demonstrate that the requirement for a 5' phosphate is conserved between *Drosophila* and human cells, but that in neither organism is an siRNA 3' hydroxyl needed. There was no evidence that RdRPs play any role whatsoever in *Drosophila* or human RNAi, despite the clear requirement for such enzymes in PTGS in plants, quelling in *Neurospora crassa*, and RNAi in *C. elegans* and *Dictyostelium discoideum* (Cogoni et al. (1999) *Nature* 399:166-169; Dalmayetal. (2000) *Cell* 101:543-553; Mourrain et al. (2000) *Cell* 101, 533-542; Smardon et al. (2000) *Curr. Biol.* 10:169-178; Sijen et al. (2001) *Cell* 107:465-476; Martens et al. (supra)). In this respect, the mechanism of RNAi in flies and mammals is distinct from that of PTGS, quelling, and RNAi in worms and *Dictyostelium*.

Example I

Requirement for the siRNA 5' Phosphate in Human RNAi

Synthetic siRNAs bearing a 5' hydroxyl can efficiently mediate RNAi both in vitro in *Drosophila* embryo lysates and in vivo in cultured human cells (Elbashir et al. (2000b supra); Elbashir et al. (2000b supra); and Nykänen et al. (supra)). However, in the *Drosophila* in vitro system, an endogenous kinase rapidly converts the 5' hydroxyl group to a phosphate (Nykänen et al. (supra)). Blocking siRNA phosphorylation by substituting the 5' hydroxyl with a methoxy moiety completely blocks RNAi in *Drosophila* embryo lysates (Nykänen et al. (supra)). Furthermore, 5' phosphorylated siRNAs more efficiently trigger RNAi in vivo in *Drosophila* embryos than do 5' hydroxyl-containing siRNAs (Boutla et al. (2001) *Curr. Biol.* 11 :1776-1780). 5' hydroxyl-containing, synthetic siRNAs that trigger RNAi in cultured mammalian cells (Elbashir et al. (2001a supra); Elbashir et al. (2002 supra)), in mice (McCaffrey et al. (2002) *Nature* 418:38-39; Lewis et al. (2002) *Nat. Genet.* 10.1038/ng.944) and perhaps even in plants (Klahre et al. (2002) 14 Aug. 2002 (10.10731pnas. 182204199) may likewise be phosphorylated by a cellular kinase prior to entering the RNAi pathway.

Figure 3A:
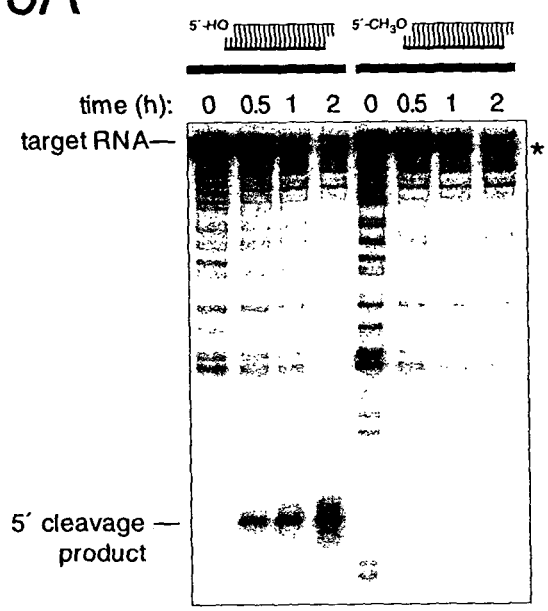
FIG. 3. The siRNA 5' phosphate group is required for siRNA-directed target cleavage in HeLa S100 extracts. (A) RNAi in vitro in human HeLa cell S100 extract. At left, a time course of in vitro RNAi for a standard siRNA; at right, for an siRNA duplex bearing a 5' methoxy guide strand. The asterisk indicates the position of a 5' cleavage product catalyzed by an endogenous, human let-7-programmed RISC complex, which cleaves this target RNA within a let-7 complementary sequence located near the 3' end of the RNA (Hutvágner and Zamore, 2002a). This cleavage product serves as an internal control. (B) Phosphorylation status of the guide strand of an siRNA duplex upon incubation in HeLa S100. An siRNA duplex containing a guide strand 3'-end-labeled with a -$_{32}$P cordycepin (3' deoxyadenosine triphosphate) was incubated in a standard HeLa S100 RNAi reaction, then analyzed on a 15% sequencing gel. Phosphorylation accelerates the gel mobility of the labeled siRNA strand, because it adds two additional negative charges. The radiolabeled RNA is 3' deoxy; therefore, we infer that the added phosphate is on the 5' end.
Figure 3B:
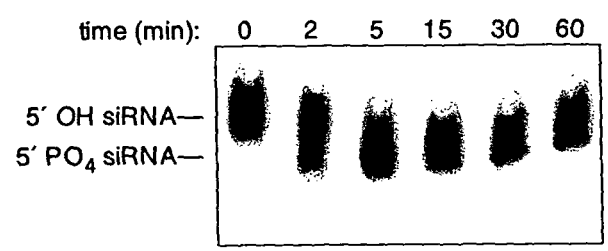

To determine if a 5' phosphate is required for RNAi in mammals, mammalian RNAi was first examined in vitro, using HeLa cell S100 extract. These reactions accurately recapitulate the known features of siRNA-directed RNAi in mammalian cell culture: exquisite sequence-specificity (Elbashir et al. (2001a supra)) and target RNA cleavage (Holen et al. (2002) *Nucleic Acids Res.* 30:1757-1766). RNAi reactions were performed in HeLa S100 extracts using siRNA duplexes in which the guide strand (i.e., the antisense strand) contained either a 5' hydroxyl or a 5' methoxy group (FIG. 2A) and a chimeric target RNA in which nucleotides 62 to 81 were complementary to the siRNA (FIG. 2B). When the guide strand of the siRNA duplex contained a 5' hydroxyl group, and could, therefore, be phosphorylated, it directed cleavage of the target RNA within the sequence complementary to the siRNA (FIG. 3). Target cleavage directed by this siRNA occurred at precisely the same site in the HeLa S100 as in *Drosophila* embryo lysate. These data suggest that endonucleolytic cleavage of the target RNA is a common feature of RNAi in flies and mammals. siRNAs with a 5' methoxy group cannot be phosphorylated by nucleic acid kinases and cannot direct RNAi in lysates of *Drosophila* embryos (Nykänen et al. (2001 supra)). Such siRNAs were likewise unable to direct cleavage of the target RNA in the HeLa S100 reaction (FIG. 3A). Although the exogenous, methoxy-blocked siRNA does not trigger RNAi in these reactions, an endogenous HeLa RISC complex that contains the miRNA, let-7 (Hutvágner and Zamore (2002) 1 Aug. 2002 (10.1126/science.1073827, cleaved the chimeric target RNA within the let-7 complementary sequence near its 3' end (FIG. 2B) in all of the human invitro RNAi reactions. This 5' cleavage product (indicated by an asterisk) serves as an internal control for the HeLa reactions. Thus, mammalian RNAi, like RNAi in *Drosophila* (Boutla et al. (2001) *Curr. Biol.* 11:1776-1780; Nykänen et al. (2001 supra)), requires the siRNA 5' phosphate for target cleavage and suggest that 5' hydroxyl-containing siRNA duplexes must be phosphorylated by a cellular kinase before they become competent to mediate RNAi in human cells. Consistent with this idea, 5' hydroxyl-containing siRNAs are rapidly 5' phosphorylated after only 5 min incubation in the HeLa S100 (FIG. 3B). Thus, like *Drosophila,* human cells contain a nucleic acid kinase that can add a 5' phosphate to a synthetic siRNA.

Example II

Role of the siRNA 3 Hydroxyl Group in Flies and Mammals

Figure 4A:
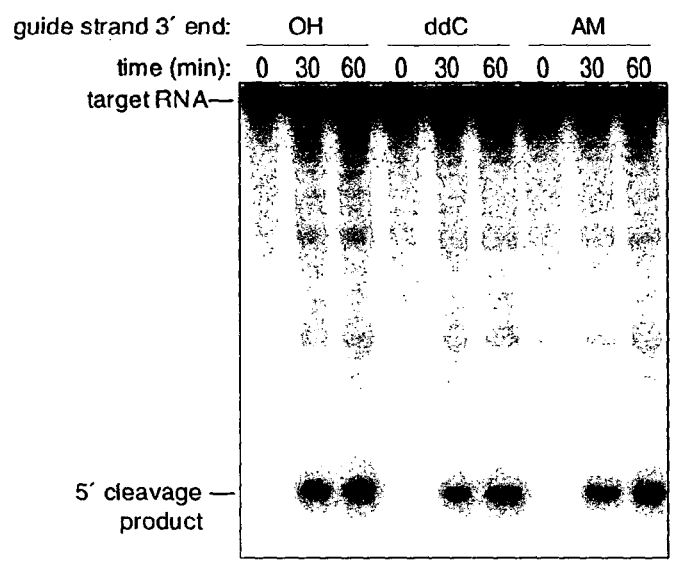
FIG. 4. The siRNA 3' hydroxyl is dispensable for siRNA-directed target cleavage in *Drosophila* and human cell extracts. (A) 3'-blocked siRNAs trigger RNAi in *Drosophila* embryo lysates with the same efficiency as 3'-hydroxyl-containing siRNAs. ddC, 2',3' dideoxy C; AM, amino modifier. (B) 3'-blocked siRNAs trigger RNAi in HeLa S100 extracts with the same efficiency as standard, 3'-hydroxyl-containing siRNAs. An over-exposure of the region of the gel containing the 5' cleavage product is shown in the lower panel. The asterisk marks the internal control 5' cleavage product described in FIG. 3.

Both siRNAs produced by enzymatic cleavage of dsRNA and those prepared by chemical synthesis contain 3' hydroxyl termini (Elbashir et al. (supra)). Experiments using nuclease-treated siRNAs suggested that a 3' phosphate blocks RNAi in *Drosophila* embryo lysates (Lipardi et al. (supra)), a finding consistent with authentication of siRNA 3' structure by the RNAi machinery, with siRNAs acting as primers for cRNA synthesis, or with RNA-templated ligation of multiple siRNAs into cRNA. To determine if the siRNA 3' hydroxyl group plays an essential role in RNAi, two siRNAs were synthesized in which the 3' hydroxyl group of the guide strand was blocked (FIG. 2). In one siRNA, the 3' hydroxyl was replaced by a 2',3' dideoxy terminus. In the other, the 3 position contained 3-amino-propyl phosphoester (3' 'amino modifier'). Each of the blocked siRNA guide strands was analyzed by electrospray mass spectrometry to confirm its identity and purity. The two modified siRNA guide strands, as well as a 3' hydroxyl-containing control strand, were annealed to a standard 21 nt siRNA sense strand. The three resulting siRNA duplexes were tested for their ability to direct cleavage of a complementary target RNA in an in vitro RNAi reaction containing *Drosophila* embryo lysate. FIG. 4A shows that the two 3'-blocked siRNAs produced the same degree of target cleavage as the 3' hydroxyl-containing siRNA control.

Figure 4B:
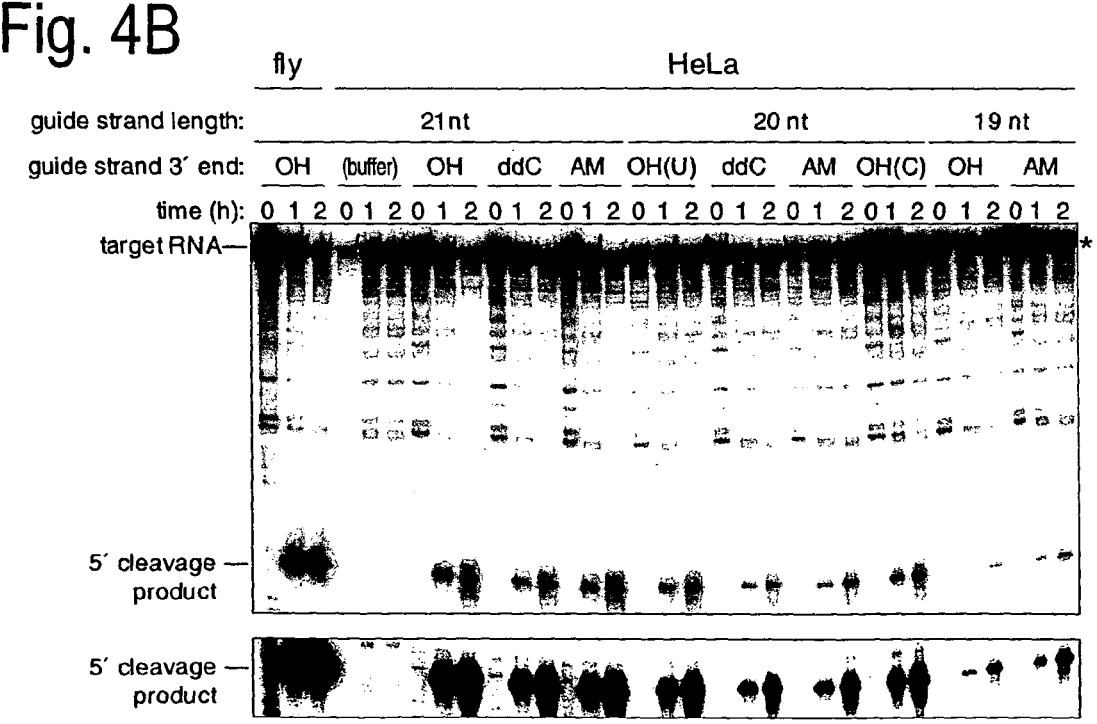

Next, the experiment was repeated in HeLa S100 extract to determine if an siRNA 3' hydroxyl group is required for RNAi in mammalian cells. 3' modification of an siRNA has been reported to be permitted for RNAi in mammalian cells (Holen et al. (supra)), but it was not shown in those experiments that all of the siRNA was 3' modified. In contrast to the 5' methoxy modification, which completely blocked target RNA cleavage in the HeLa S100 reaction, 3' modification had no effect on the efficiency or specificity of RNAi (FIG. 4B). The identity and purity of these siRNAs was confirmed by electrospray mass spectrometry. However, it could be envisioned that a fraction of the siRNA guide strand was cleaved within the single-stranded, two nucleotide, 3' overhang by a nuclease in the HeLa S100, regenerating the 3' hydroxyl. If this occurred, the cleaved siRNAs could then act as primers. To exclude this possibility, RNAi reactions were performed using progressively shorter guide siRNAs blocked at the 3' end by either a 2',3' dideoxy or a 3' amino modifier group. The 20 or 19 nt guide strands were annealed to the same 21 nt sense siRNA strand. FIG. 4B shows that target RNA cleavage occurred in all cases, although the efficiency of cleavage decreased as the siRNA guide strand was shortened, even when it contained a 3' hydroxyl terminus. If the 3' blocked 21 nt siRNA was active because it had been shortened to a 20-mer, it could not have attained the activity of the 3' hydroxyl 21 nt siRNA. Similarly, if nucleolytic removal of the 3' block accounted for the activity of the 20 nt guide siRNA, it should have only been as active as the 19 nt, 3' hydroxyl-containing siRNA. These results suggest that the 3' hydroxyl group of the siRNA guide strand does not play an obligatory role in siRNA-directed RNAi in flies or mammals.

Example III

Single-stranded siRNAs

Current models for RNAi, including those that propose siRNA to function as guides for an endonuclease and models that propose siRNAs to act as primers for target-RNA templated RNA synthesis, predict that siRNAs ultimately function as single strands. In fact, in *Drosophila* embryos, single-stranded antisense siRNAs corresponding to the Notch mRNA elicited Notch phenotypes in 12% of injected embryos, although the expressivity was quite low (Boutla et al. (2001, supra)). Furthermore, single-stranded RNAs of various lengths trigger RNAi in *C. elegans*, but only when they contain a 3' hydroxyl group, suggesting that single-stranded siRNA functions in that organism as a primer for an RdRP (Tijsterman et al. (2002, supra). Consistent with single-stranded siRNAs acting in nematodes as primers that direct the production of new dsRNA, they fail to trigger RNAi in the absence of Dicer (Dcr-1) (Tijsterman et al. (2002, supra)).

Figure 5A:
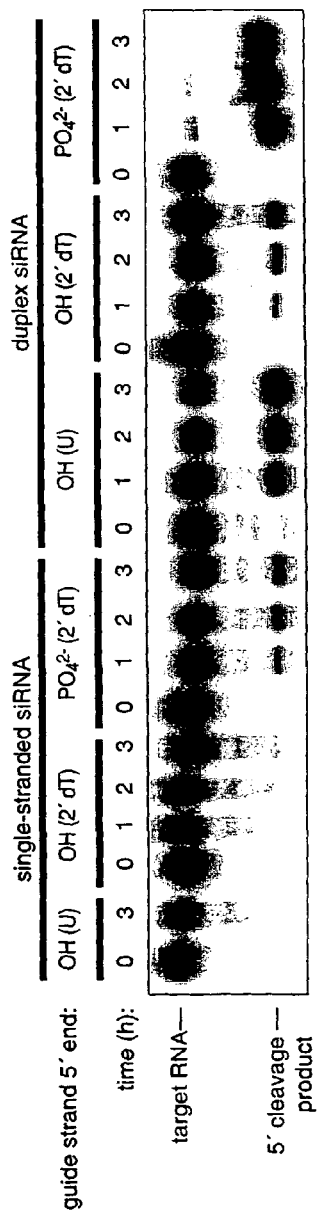
FIG. 5. Single-stranded siRNA guides target cleavage in *Drosophila* embryo lysates. (A) Single-stranded siRNAs with the sequence of the miRNA let-7 triggered target cleavage in *Drosophila* embryo lysate, but only if the 5' end was pre-phosphorylated. (B) Single-stranded siRNAs complementary to firefly luciferase sequence triggered target cleavage in *Drosophila* embryo lysate, even if the 3' end was blocked (2',3'ddC). No target cleavage was observed using an siRNA with a 5' methoxy group. (C) Rate of degradation of single-stranded siRNA in the *Drosophila* embryo lysate. siRNA single-strands were 3' end-labeled with a—$_{32}$P cordycepin and their stability measured with (filled circles) or without (open squares) a 5' phosphate. The curves represent the best-fit to a single exponential, consistent with pseudo first-order kinetics for single-stranded siRNA decay. The difference in rates is 1.4-fold (with versus without a 5' phosphate).

It was next examined if the guide siRNA strand alone could trigger target cleavage in an in vitro RNAi reaction containing either *Drosophila* embryo lysate or human HeLa cell S100. First, it was examined whether single-stranded siRNA could direct target RNA cleavage in *Drosophila* embryo lysates (FIG. 5A). For this experiment, siRNA was used having the sequence of the miRNA let-7 (FIG. 2A). Cleavage of the target RNA (FIG. 2B) by a let-7-containing siRNA duplex produces a diagnostic 522 nt 5' product (Hutvágner and Zamore, 2002a). When the synthetic siRNA was used as a single strand, the target RNA was not cleaved (FIG. 5A). Similarly, a single-stranded siRNA of the same sequence but bearing a 2' deoxy thymidine (dT) instead of uracil as its first nucleotide, was also a poor trigger of target cleavage. However, both these siRNAs contain a 5' hydroxyl, and a 5' phosphate is required for siRNA duplexes to trigger target RNA cleavage in *Drosophila* embryo lysates (Nykänen et al., 2001). It was thus hypothesized that the defect with the single-stranded siRNAs might be that they lacked a 5' phosphate and cannot obtain one because they are not substrates for the *Drosophila* kinase. In support of this hypothesis, when the single-stranded siRNA starting with dT was pre-phosphorylated with polynucleotide kinase, it directed target cleavage.

Figure 5C:
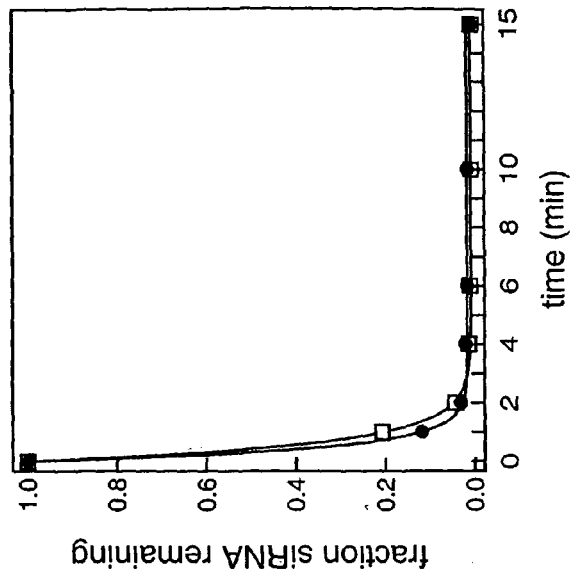
Figure 5B:
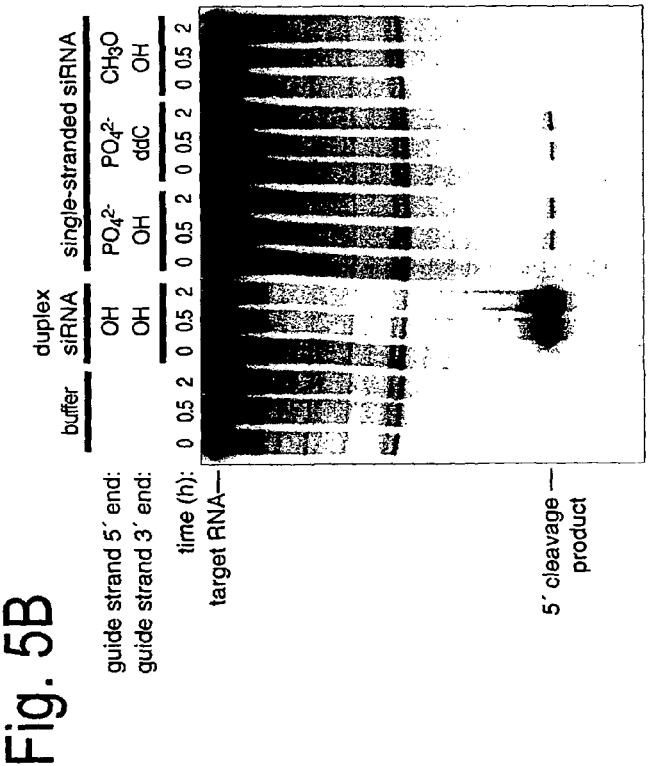

To confirm these findings, the activity of a second single-stranded siRNA, complementary to the luciferase portion of the target RNA, was examined. When pre-phosphorylated, this single-stranded siRNA again directed target cleavage in *Drosophila* embryo lysate, albeit less efficiently than the same molar concentration of an siRNA duplex (FIG. 5B). Cleavage occurred at precisely the same site in the target RNA for both single-stranded and double-stranded siRNAs, suggesting that the single-stranded siRNA entered the RNAi pathway, rather than triggered RNA destruction by a different route. The same single-stranded siRNA sequence bearing a 5' methoxy group did not direct target RNA cleavage (FIG. 5B). Together, the experiments in FIG. 5 demonstrate that single-stranded siRNAs, like the guide strands of siRNA duplexes, do not function in the RNAi pathway unless they bear a 5' phosphate.

To determine if single-stranded siRNAs trigger target destruction in *Drosophila* embryo lysates by acting as primers, the 3' end of the siRNA to 2',3' dideoxy was modified. As with double-stranded siRNAs, blocking the 3' end of the single-stranded siRNA had no effect on the efficiency or specificity with which the target was cleaved (FIG. 5B). It should be noted that the efficiency of target cleavage by single-stranded siRNAs is significantly less than that of siRNA duplexes. The lower efficiency might simply reflect the remarkably short lifespan of single-stranded siRNA in the *Drosophila* embryo lysate: the vast majority is destroyed within the first 2 min of incubation. One explanation for the requirement for a 5' phosphate might be that without it, the single-stranded siRNA is destroyed even faster. This explanation is unlikely, because the rate of single-stranded RNA destruction is only 1.4-fold faster for 5' hydroxy siRNAs (FIG. 5C). More likely is that the 5' phosphate of the single-stranded siRNA is required for its entry into the RISC, and that because a small fraction of 5' phosphorylated, single-stranded siRNA enters the RISC it is protected from degradation, enhancing its stability in the lysate.

Figure 6A:
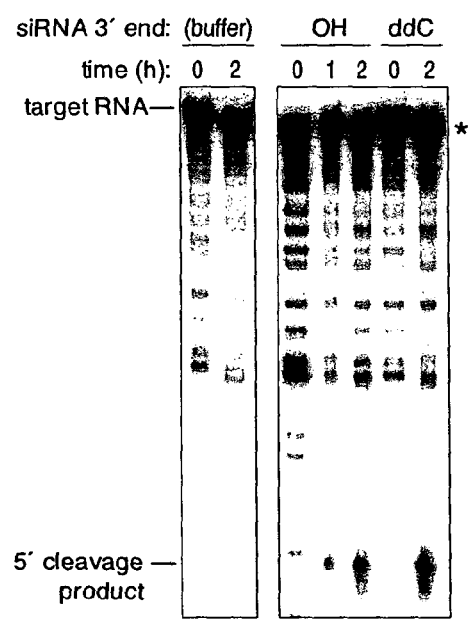
FIG. 6. A 5' phosphate, but not a 3' hydroxyl is required for single-stranded antisense siRNAs to trigger RNAi in HeLa S100 extract. (A) Single-stranded siRNA triggered target cleavage in HeLa S100, even if the 3' end of the siRNA was blocked (2',3' dideoxy). (B) Blocking the 5' end of the siRNA with a methoxy group eliminated the ability of the single-stranded RNA to trigger RNAi. The asterisk marks the control 5' cleavage product described in FIG. 3.
Figure 6B:
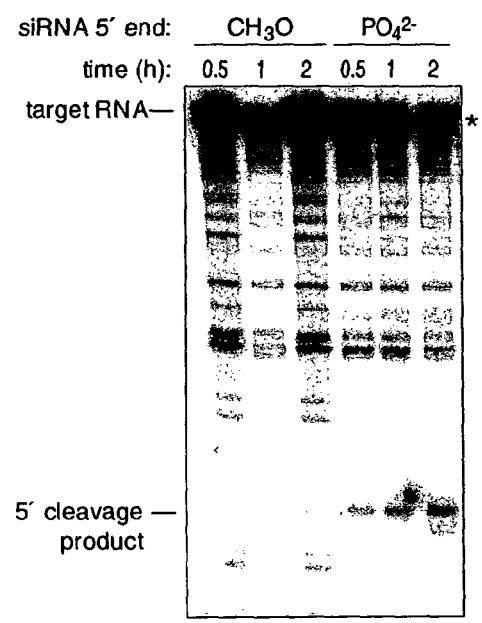

Next, it was examined whether single-stranded siRNAs could function to trigger RNAi in HeLa S100 extracts. Again, single-stranded siRNAs directed target cleavage at the same site as the corresponding siRNA duplex (FIG. 6A). Pre-phosphorylation of single-stranded siRNA was not required for it to function in target cleavage in HeLa S100, but blocking the 5' end with a methoxy group completely eliminated RNAi (FIG. 6B). These results suggest that a 5' phosphate is required for mammalian RNAi, but that the nucleic acid kinase(s) responsible for phosphorylating siRNAs in HeLa S100 acts on single-stranded siRNA, unlike its *Drosophila* counterpart. Blocking the 3' end of the single-stranded siRNA had no effect on the ability of the single-stranded siRNA to cleave the target RNA in HeLa S100 (FIG. 6A). Thus, the structural requirements for single-stranded siRNA function in target cleavage are conserved between flies and mammals: a 5' phosphate is required, but a 3' hydroxyl is not.

Together these data support the view that siRNAs do not direct target RNA destruction by priming the synthesis of new RNA, nor are siRNAs ligated together to generate cRNA. Both processes should require a 3' hydroxyl group, which is dispensable for target cleavage in either *Drosophila* or human cell extracts. Instead, the data suggest that siRNAs act as guides to direct a protein endoribonuclease to cleave the target RNA. The finding that single-stranded siRNAs can function as guides in the RNAi pathway suggests that each individual RISC contains only one siRNA strand. Consistent with this view, in HeLa cell S100 extracts, the single stranded miRNA, let-7, is in an endogenous RISC that catalyzes multiple rounds of cleavage of a perfectly complementary target RNA (Hutvágner and Zamore, 2002a).

Previously, it was proposed that the siRNA 5' phosphate was recognized twice during the assembly of the siRNA-containing endoribonuclease complex (Nykänen et al., 2001). That study placed one 5' phosphate recognition event before siRNA duplex unwinding, but could not distinguish whether the 5' phosphate is required subsequently at the unwinding step itself or after unwinding is complete. The absence of target cleavage by single-stranded siRNAs lacking a 5' phosphate suggests that the second phosphate recognition step occurs after the siRNA duplex is unwound. In both *Drosophila* embryo lysates and human HeLa S100, cleavage directed by single-stranded siRNA was less efficient than RNAi triggered by siRNA duplexes. This inefficiency correlated with the general instability of short RNA in the in vitro extracts, as determined by measuring single-stranded siRNA half-life using 3' radiolabeled siRNAs (FIG. 5C) and by Northern hybridization.

Example IV siRNAs do not Function as Primers in HeLa Cells

To assess if the above-described in vitro results accurately predict the RNAi mechanism in vivo, cultured human cells were used to assess the structural requirements for siRNA function. Synthetic siRNAs were co-transfected into HeLa cells with plasmids expressing target (*Photinus pyralis*, Pp) and control (*Renilla reniformis*, Rr) luciferase mRNAs. Luciferase expression was measured, and target (firefly) luciferase levels were normalized to the *Renilla* control. The results of these experiments are shown in FIG. 7.

First, the requirement for a 5' phosphate observed in *Drosophila* and HeLa extracts was conserved in vivo (FIG. 7A). A 5' hydroxyl-containing siRNA duplex triggered efficient gene silencing in vivo, reducing expression of the target luciferase >90%. In contrast, a 5' methoxy-modified siRNA reduced firefly luciferase levels by only two-fold. This small reduction may reflect inhibition of translation, perhaps by an anti-sense mechanism. Alternatively, some of the methoxy-blocked siRNA may inefficiently enter the RNAi pathway in vivo. An siRNA in which the guide strand contained a 5' amino modifier group, 6-amino-hexyl phosphoester, was significantly more effective in suppressing target mRNA expression than the siRNA with the 5' methoxy group (FIG. 7A). This finding is consistent with the idea that a 5' phosphate group is required for siRNA function, but that the 5' phosphate participates in non-covalent interactions only, since the modified 5' phosphate should be less able to act as an electron acceptor. The in vivo studies agree with the in vitro results: a 5' phosphate is essential for efficient siRNA function in flies and mammals. However, in flies only duplex siRNAs can be 5' phosphorylated by cellular kinases, whereas in mammals, both single-stranded and double-stranded siRNAs are phosphorylated.

Consistent with the view that the core function of siRNA in human cells is as guides, not primers, blocking the 3' end of the siRNA guide strand had no effect on RNAi in vivo. siRNA duplexes in which the guide strand contained a 3' hydroxyl, a 2',3' dideoxy, or a 3' amino modifier were all equally effective in triggering RNAi in vivo (FIG. 7A). The silencing activity in vivo of a 21-nt, 3'-blocked siRNA guide strand was greater than that of a 20-nt, 3' hydroxy siRNA guide strand, indicating that the 3' block was not removed in vivo. It is believed that these data exclude an obligatory role for the siRNA 3' hydroxyl group in RNAi in mammalian cells, and argue that siRNAs do not normally trigger target destruction in human cells by functioning as primers.

These experiments were conducted at siRNA concentrations where the siRNA is not limiting for RNA silencing. An siRNA function in priming the synthesis of dsRNA might be used when siRNAs are limiting. Therefore, the relative ability of siRNA duplexes in which the guide strand either contained a 3' hydroxyl or a 2',3' dideoxy group at low siRNA concentrations was tested (FIG. 7B). It was found that the efficacy of the two types of siRNAs did differ when siRNA was rate limiting for target mRNA silencing, but never by more than 1.8-fold. The observed difference in efficacy between the two types of siRNAs is not sufficiently great to support the view that the 3' hydroxyl group of the siRNA is used to prime the synthesis of dsRNA from the target mRNA. If the siRNA were used to prime dsRNA synthesis, the production of new dsRNA by an RdRP using the siRNA as a primer should have amplified the silencing activity of the 3' hydroxy but not the 2',3' dideoxy siRNA at limiting concentrations. To further exemplify, if the 3' hydroxy guide strand had primed synthesis of one molecule of dsRNA (~130 bp long based on the site of siRNA/target complementarity) for each target mRNA molecule, and this new dsRNA was then "Diced" into just two of the possible six new siRNAs, at least a two-fold difference between the two siRNAs should have been observed. This analysis even further fails to account for the new crop of siRNAs acting in a subsequent cycle of priming, which would further amplify the difference between 3' deoxy and 3' hydroxy siRNA at limiting concentrations. The simplest interpretation of the above findings that 3' hydroxy siRNAs trigger no significant amplification of RNA silencing relative to 3' blocked siRNAs is that an siRNA-primed, RdRP-dependent cycle of siRNA amplification plays no productive role in RNAi in cultured HeLa cells, even at low siRNA concentrations. The small difference in efficacy between 3' OH and 2',3' dideoxy siRNAs likely indicates that the blocked siRNAs have a subtle defect such as a lower affinity for components of the RNAi machinery, slightly reduced intracellular half-life, or a minor reduction in phosphorylation rate. This defect may result from the 2' deoxy modification of the terminal nucleotide, rather than the 3' block, since siRNAs with 2' deoxythymidine tails have been reported to be less efficient than those containing uracil in HeLa cells (Hohjoh (2002) *FEBS Letts.* 521:195-199).

The above in vitro studies indicate that single-stranded siRNAs can enter the RNAi pathway, albeit inefficiently. To test if single-stranded siRNAs could trigger mRNA silencing in vivo, various concentrations of single-stranded, sense or antisense siRNA were substituted for siRNA duplexes in HeLa cell co-transfections (FIG. 8A). As the concentration of antisense single strand was increased, the expression of the firefly luciferase decreased relative to the *Renilla* internal control. Single-stranded siRNAs were less efficient than siRNA duplexes: it took nearly 8-times more single-stranded siRNA to approach the potency of the corresponding duplex. This inefficiency may simply reflect rapid degradation of the majority of the transfected single-stranded siRNA before it can enter the RISC complex. Cells may possess a mechanism that stabilizes siRNA duplexes and shuttles them to the RISC as single-strands without exposing them to degradatory enzymes. Thus, if endogenous siRNAs are double-stranded in vivo, they may be double-stranded so as to facilitate their entry into the RNAi pathway and to exclude them from a competing pathway that degrades small, single-stranded RNA. Alternatively, single-stranded siRNAs may bypass a key step in RISC assembly, making them less efficient than duplexes in triggering RNAi. The dramatic instability of single-stranded siRNAs in vitro may simply reflect their inefficiency in assembling into a RISC, which could protect them from degradation.

Gene silencing by single-stranded siRNA was sequence-specific, and single-stranded sense siRNA did not alter the expression of the target RNA (FIG. 8B). Thus, it is unlikely that siRNAs themselves are copied by an RdRP in mammalian cells, since copying the sense siRNA should generate the anti-sense siRNA strand. However, copying sense siRNA into a duplex would not generate the characteristic 3' overhanging ends of siRNAs. Such 3' overhangs might be required for siRNA unwinding and/or efficient RISC assembly. Pre-phosphorylation of single-stranded siRNA did not enhance its potency in HeLa cells, consistent with the observations in HeLa S100 extracts, but blocking phosphorylation with a 5' methoxy group abolished silencing, pointing to the importance of 5' phosphorylation for single-stranded siRNA function in vivo (FIG. 8B). The exemplified findings are not entirely unexpected, since endogenous, single-stranded miRNAs enter the RNAi pathway in HeLa cells (Hutvágner and Zamore, (2002a supra). In particular, the finding that single-stranded siRNAs can elicit RNA silencing blurs the distinction between RNAi and antisense effects. The above data evidence that single-stranded siRNAs trigger the same pathway as siRNA duplexes: both guide endonucleolytic cleavage of target RNAs at the same site, and both require 5' phosphates, but not 3' hydroxyl groups, to function. The data support the view that single-stranded siRNAs function in the same pathway as siRNA duplexes, the RNAi pathway.

The in vitro experiments with Drosophila embryo lysates and HeLa S100 extracts and in vivo experiments in HeLa cells argue against siRNAs functioning as primers in the RNAi pathway. These findings are consistent with the absence of any genes encoding canonical RdRPs in the currently available release of either the Drosophila or human genome. A hallmark of the involvement of RdRPs in post-transcriptional silencing is the spread of silencing beyond the confines of an initial trigger dsRNA or siRNA into regions of the target RNA 5' to the silencing trigger. In C. elegans, this spreading ('transitive RNAi') is manifest in the production of new siRNAs corresponding to target sequences not contained in the exogenous trigger dsRNA (Sijen et al. (2001, supra)). Furthermore, small RNAs as long as 40 nt can initiate silencing in worms, but only if they contain 3' hydroxyls, suggesting that they act as primers for the synthesis of cRNA (Tijsterman et al. (2002, supra). In contrast, 5' spreading is not detected in Drosophila, either in vitro (Zamore et al. (2000, supra)), in cultured Drosophila S2 cells (Celotto and Graveley, (2002, supra)), or in vivo in flies. The data support the view that, in both flies and mammals, siRNAs trigger target RNA destruction not by acting as primers, but rather by guiding a protein endoribonuclease to a site on the target RNA that is complementary to one strand of the siRNA. The observation that the target cleavage site is across from the center of the complementary siRNA (Elbashir et al. (2001c, supra); Elbashir et al. (2001b, supra)) is consistent with an enzyme other than Dicer acting in target RNA destruction and not with models that propose that Dicer destroys target RNAs. Furthermore, mammalian extracts depleted of Dicer still catalyze siRNA-directed target cleavage (Martinez et al. (2002, in press).

Previous concerns have been raised regarding the possibility of designing siRNAs capable of degrading a particular mRNA isoform that differs from other isoforms in only a small region of sequence, perhaps a single nucleotide. If siRNAs do not act as RdRP primers in flies and mammals, then there is no fear that the silencing signal will spread 5' to a region of sequence common to the entire family of mRNAs. Thus, despite earlier concerns that such siRNAs would not be possible (Nishikura, 2001), these data suggest that isoform- and polymorphism-specific siRNAs can be designed for use in mammals to dissect the function of individual gene isoforms and also for therapeutic use to treat, for example, inherited autosomal dominant human diseases.

The above examples demonstrate that the anti-sense strand of an siRNA can function in RNAi in vitro in Drosophila or human cell extracts in the absence of the sense siRNA strand. These single-stranded siRNAs only function if they are 5' phosphorylated. 5' phosphorylated, single-stranded siRNA directed target RNA cleavage in Drosophila embryo lysates, albeit less efficiently than the same molar concentration of the corresponding siRNA duplex. Cleavage of a target RNA in response to a 5' phosphorylated, single-stranded siRNA occurred at precisely the same site in the target as was observed for a standard siRNA duplex. Thus, single-stranded siRNA enters the RNAi pathway. The 2' and 3' positions of the siRNA terminus are amenable to chemical modification, since modifying the 3' end of the siRNA to 2',3' dideoxy does not impair its function. Thus, it is now possible to introduce specific chemical modifications into the single-stranded siRNA to enhance its in vivo stability. The requirement for a 5' phosphate is absolute, since blocking 5' phosphorylation of the single-stranded siRNA by introducing a 5' methoxy group completely eliminated its ability to direct target RNA cleavage. Modification of the 5' most nucleotide of an siRNA antisense strand from ribo to 2' deoxy was previously shown to inhibit phosphorylation of the siRNA in Drosophila embryo lysates. However, pre-phosphorylating the 5' end of this 2' deoxy-containing siRNA allows it to function as a single-strand. Thus, 5' modifications of the single-stranded siRNA are also possible, as long as the single-stranded siRNA is 5' phosphorylated.

In both Drosophila embryo lysates and human HeLa S100, cleavage directed by single-stranded siRNA was less efficient than RNAi triggered by siRNA duplexes. This inefficiency correlated with the general instability of short RNA in the in vitro extracts, as determined by measuring single-stranded siRNA half-life using 3' radiolabeled siRNAs and by using Northern hybridization. If siRNAs siRNAs are double-stranded in vivo, they may be double-stranded so as to facilitate their entry into the RNAi pathway and to exclude them from a competing pathway that degrades small, single-stranded RNA. Thus, a preferred aspect of the invention features single-stranded siRNAs which have been modified so as to enhance their in vivo stability, while still retaining their function in triggering sequence-specific RNAi.

Key improvements over the prior art include, but are not limited to, the following: (1) single-stranded siRNAs are smaller, less complicated and less expensive to produce than siRNA duplexes; and (2) chemically-modified anti-sense RNA oligonucleotides (single-stranded siRNAs) trigger RNA interference in an efficient, naturally-occurring cellular pathway for the targeted destruction of an mRNA. Chemical modification of single-stranded siRNA is compatible with its function and enhances siRNA stability. The single-stranded siRNAs of the instant invention are particularly useful in, for example, functional genomics and drug target validation. Moreover, the modified single-stranded siRNAs of the instant invention are useful therapeutically in targeting genes of interest in vivo for RNA interference.

Experimental Procedures

General Methods

Drosophila embryo lysate preparation, in vitro RNAi reactions, and cap-labeling of target RNAs using Guanylyl transferase were carried out as previously described (Zamore et al. (supra)). Human S100 extracts were prepared as described (Dignam et al. (1983) Nucleic Acids Res. 11:1475-1489). HeLa S100 was substituted for Drosophila embryo lysate in an otherwise standard RNAi reaction, except that incubation was at 37° C. instead of 25° C. Cleavage products of RNAi reactions were analyzed by electrophoresis on 8% denaturing acrylamide gels. Gels were dried, exposed to image plates (Fuji), which were scanned with a Fuji FLA-5000 phosphorimager. Images were analyzed using Image Reader FLA-5000 version 1.0 (Fuji) and Image Gauge version 3.45 (Fuji).

siRNA Preparation

Synthetic RNAs (Dharmacon) were deprotected according to the manufacturer's protocol and processed as previously described (Nykänen et al. (supra)). siRNA strands were annealed (Elbashir et al. (supra)) and used at 100 nM final concentration unless otherwise noted. siRNA single strands were phosphorylated with polynucleotide kinase (New England Biolabs) and 1 mM ATP according to the manufacturer's directions.

Tissue Culture siRNA transfections were as described (Elbashir et al. (supra)). Briefly, HeLa cultured cells were propagated in Dulbecco's modified Eagle's medium (DMEM) supplemented with 10% fetal bovine serum (FBS) and 1% penicillin/streptomycin (Life Technologies). Cells were trypsinized and seeded at 1×10 5 cells/ml in 24 well plates (5×10 4 cells/well). Twenty four hours after seeding, 1 mg pGL2 control firefly luciferase (Pp-luc GL2; Promega) and 0.1 mg pRL-TK *Renilla* luciferase (Rr-luc; Promega) plasmids and the luciferase siRNA (25 nM) were co-transfected with LipofectAMINE 2000 reagent (Invitrogen) in DMEM (Life Technologies) lacking serum and antibiotics according to manufacturer's instructions. Media was replaced 4 h after transfection with DMEM containing 10% fetal bovine serum (Life Technologies), and cells were lysed 2 days after transfections in 1× Passive Lysis Buffer (Promega) according to the manufacturer's instructions. Luciferase expression was determined by the Dual luciferase assay kit (Promega) using a Mediators PhL luminometer. Data analysis was performed using Excel (Microsoft) and IgorPro 5.0 (Wavemetrics). All experiments were performed in triplicate, and error was propagated through all calculations.

Equivalents

Those skilled in the art will recognize, or be able to ascertain using no more than routine experimentation, many equivalents to the specific embodiments of the invention described herein. Such equivalents are intended to be encompassed by the following claims.

---

What is claimed:

1. A method of activating target-specific RNA interference (RNAi) in a mammalian cell in vitro, comprising introducing into said cell an isolated, single-stranded small interfering RNA molecule (ss-siRNA) having a length of 19-21 nucleotides, wherein the sequence of said ss-siRNA molecule is complementary to a target mRNA sequence and directs target-specific RNA interference (RNAi) and wherein the 5' nucleotide is 5' phosphorylated or is capable of being 5' phosphorylated in vitro, said ss-siRNA being introduced in an amount sufficient for degradation of the target mRNA to occur, thereby activating target-specific RNAi in the cell.

2. The method of claim 1, wherein the ss-siRNA is introduced into the cell by contacting the cell with the ss-siRNA.

3. The method of claim 2, wherein the ss-siRNA is introduced into the cell by contacting the cell with a composition comprising the ss-siRNA and a lipophillic carrier.

4. The method of claim 1, wherein the target mRNA specifies the amino acid sequence of a protein involved or predicted to be involved in a human disease or disorder.

5. The method of claim 1, wherein degradation of the target mRNA produces a loss-of-function phenotype.

6. The method of claim 1, wherein the ss-siRNA is modified by the substitution of the 3'-OH of the 3' most nucleotide.

7. The method of claim 1, wherein the 3' most nucleotide has a 3'-OH replaced by a 2', 3' dideoxy terminus or an amino modifier group.

8. The method of claim 1, wherein the ss-siRNA has a length of 19 nucleotides.

9. The method of claim 1, wherein the ss-siRNA has a length of 20 nucleotides.

10. The method of claim 1, wherein the ss-siRNA has a length of 21 nucleotides.

11. The method of claim 1, wherein the 5' nucleotide of the ss-siRNA is 5' phosphorylated with a phosphate groups selected from the group consisting of a momophosphate, a diphosphate and a triphosphate.

* * * * *